United States Patent [19]

Weber et al.

[11] 4,314,820
[45] Feb. 9, 1982

[54] DISTYRYLBENZENE FLUORESCENT BRIGHTENING AGENTS

[75] Inventors: Kurt Weber, Basel; Hans R. Meyer, Binningen, both of Switzerland

[73] Assignee: Ciba-Geigy Corporation, Ardsley, N.Y.

[21] Appl. No.: 136,615

[22] Filed: Apr. 2, 1980

[30] Foreign Application Priority Data

Apr. 11, 1979 [CH]  Switzerland .......................... 3479/79
Jun. 26, 1979 [CH]  Switzerland .......................... 5951/79

[51] Int. Cl.³ ............................................. C09K 11/06
[52] U.S. Cl. ..................................... 8/648; 252/8.75; 252/8.8; 252/8.9; 252/89.1; 252/301.21; 252/301.26; 546/255; 564/82; 564/286
[58] Field of Search .......... 8/648; 252/301.26, 301.21, 252/8.6, 544, 89.1, 8.75, 8.8, 8.9; 546/255; 564/82, 286

[56] References Cited

U.S. PATENT DOCUMENTS

| | | | |
|---|---|---|---|
| 3,271,321 | 9/1966 | Stilz et al. | 252/301.21 |
| 3,755,446 | 8/1973 | Scheuermann et al. | 560/37 |
| 3,843,718 | 10/1974 | Lueth | 560/59 |
| 3,904,678 | 9/1975 | Scheuermann et al. | 568/631 |
| 3,927,119 | 12/1975 | Luethi | 568/643 |
| 4,009,193 | 2/1977 | Scheuermann et al. | 560/251 |

FOREIGN PATENT DOCUMENTS

| | | |
|---|---|---|
| 1923267 | 11/1970 | Fed. Rep. of Germany . |
| 2039993 | 2/1972 | Fed. Rep. of Germany . |
| 2364396 | 7/1975 | Fed. Rep. of Germany . |
| 2721730 | 12/1977 | Fed. Rep. of Germany . |
| 913735 | 12/1962 | United Kingdom . |
| 1351489 | 5/1974 | United Kingdom . |
| 1522576 | 8/1978 | United Kingdom . |

OTHER PUBLICATIONS

Venkataraman's "The Chemistry of Synthetic Dyes", vol. V (Academic Press, 1971), pp. 562–565.

*Primary Examiner*—A. Lionel Clingman

*Attorney, Agent, or Firm*—John P. Spitals; Edward McC. Roberts

[57] ABSTRACT

The distyrylbenzenes of the formula

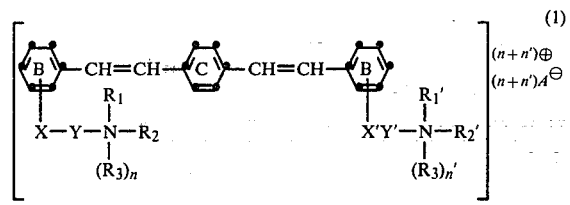

in which X and X' independently of one another are —COO— or —CON(R₄)— in the o-position, a direct bond, oxygen, sulfur, —O—C₁₋₃—alkylene—CON(R₄)—, —SO₂N(R₄)—, —O—C₁₋₃-alkylene—COO— or —OCO—, Y and Y' independently of one another are C₁₋₂₀-alkylene, R₁ and R₁' independently of one another are unsubstituted or substituted C₁₋₈-alkyl or C₃₋₄-alkenyl, or R₁ together with R₂, or R₁' together with R₂', is a heterocyclic ring, R₂ and R₂' independently of one another are unsubstituted or substituted C₁₋₈-alkyl or C₃₋₄-alkenyl, or R₂ together with R₁, or R₂' together with R₁', is a heterocyclic ring, or R₁ and R₂, or R₁' and R₂', together with R₃ are a pyridine or picoline ring, R₃ is hydrogen, unsubstituted or substituted C₁₋₄-alkyl or C₃₋₄-alkenyl, or together with R₁ and R₂ or with R₁' and R₂' is a pyridine or picoline ring, R₄ is hydrogen or unsubstituted or substituted C₁₋₁₆-alkyl, A⊖ is a colorless anion and n and n' independently of one another are the number 0 or 1, and the benzene nuclei B and C can also be substituted by non-chromophoric substituents, can be prepared by reacting a correspondingly substituted benzaldehyde with a p-xylylenephosphonate and then alkylating or protonising the distyrylbenzenediamine formed. The distyrylbenzenes are fluorescent brightening agents for organic materials. They are particularly suitable for use as additives to textile and laundry after-treatment agents which contain cationic textile softeners.

25 Claims, No Drawings

DISTYRYLBENZENE FLUORESCENT BRIGHTENING AGENTS

The present invention relates to novel distyrylbenzenes, processes for their preparation and their use for the fluorescent brightening of organic material and also to detergents containing such distyrylbenzenes.

Water-soluble 1,4-distyrylbenzenes substituted in the benzene nuclei have been disclosed in the literature, for example in German Offenlegungsschrift 1,923,267 and 2,721,730, but these are not compatible with cationic textile assistants. Furthermore, water-soluble 1,4-distyrylbenzenes with cationic substituents have been disclosed in German Offenlegungsschrift 2,364,396, but despite their cationic character these give unsatisfactory results when used in a cationic medium.

Distyrylbenzenes have now been found which do not have these disadvantages.

The invention therefore relates to novel distyrylbenzenes of the formula

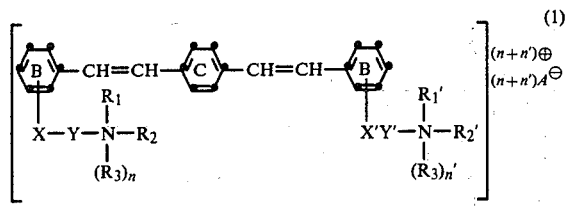

in which X and X' independently of one another are —COO— or —CON($R_4$)— in the o-position, a direct bond, oxygen, sulfur, —O—$C_{1-3}$-alkylene—CON($R_4$)—, —$SO_2$N($R_4$)—, —O—$C_{1-3}$-alkylene—COO— or —OCO—, Y and Y' independently of one another are $C_{1-20}$-alkylene, $R_1$ and $R_1'$ independently of one another are unsubstituted or substituted $C_{1-8}$-alkyl or $C_{3-4}$-alkenyl, or $R_1$ together with $R_2$, or $R_1'$ together with $R_2'$, is a heterocyclic ring, $R_2$ and $R_2'$ independently of one another are unsubstituted or substituted $C_{1-8}$-alkyl or $C_{3-4}$-alkenyl, or $R_2$ together with $R_1$, or $R_2'$ together with $R_1'$, is a heterocyclic ring, or $R_1$ and $R_2$, or $R_1'$ and $R_2'$, together with $R_3$ are a pyridine or picoline ring, $R_3$ is hydrogen, unsubstituted or substituted $C_{1-4}$-alkyl or $C_{3-4}$-alkenyl, or together with $R_1$ and $R_2$ or with $R_1'$ and $R_2'$ is a pyridine or picoline ring, $R_4$ is hydrogen or unsubstituted or substituted $C_{1-6}$-alkyl, $A^\ominus$ is a colourless anion and n and n' independently of one another are the number 0 or 1, and the benzene nuclei B and C can also be substituted by non-chromophoric substituents.

The alkylene radicals Y and Y' can be different and straight-chain or branched and preferably contain 1 to 12 and especially 1 to 6 C atoms; they can also each carry a hydroxyl group.

Suitable alkyl radicals $R_1$, $R_1'$, $R_2$ and $R_2'$ are those having 1 to 8 and preferably 1 to 4 C atoms. They can be substituted, for example by halogen, cyano, hydroxyl, alkoxy, phenyl or alkoxycarbonyl having 1 to 4 C atoms.

The radicals $R_1$ and $R_2$ together, or $R_1'$ and $R_2'$ together, can each form a 5-membered to 7-membered heterocyclic ring, for example a piperidine, pyrrolidine, hexamethyleneimine, pyridine, triazole, imidazole or morpholine ring, which can be substituted by alkyl groups having 1 to 4 C atoms.

An alkyl radical $R_4$ preferably has 1 to 4 C atoms and can be substituted, for example, by cyano, carbamoyl, carbalkoxy, hydroxyl, halogen or alkoxy having 1 to 4 C atoms.

Examples of non-chromophoric substituents of the benzene rings B and C are: halogen atoms; alkyl groups; cycloalkyl groups; alkenyl groups, alkoxy groups, alkenyloxy groups or sulfonyl groups, for example alkyl- or phenyl-sulfonyl groups, carbalkoxy groups, carbamoyl groups and sulfamoyl groups and also the substituents required to make up a carbocyclic 5-membered or 6-membered ring.

Distyrylbenzenes according to the invention which are worthy of particular mention are those of the formula

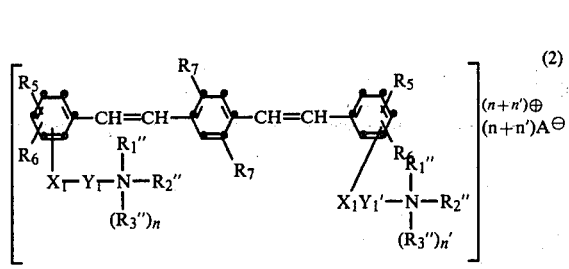

in which $X_1$ is —COO— or —CONH— in the o-position, a direct bond, oxygen, sulfur, —O—$C_{1-3}$-alkylene—CONH—, —$SO_2$NH—, —O—$C_{1-3}$-alkylene—COO— or —OCO—, $Y_1$ and $Y_1'$ independently of one another are $C_{1-4}$-alkylene or hydroxypropylene, $R_1''$ and $R_2''$ independently of one another are $C_{1-4}$-alkyl or together are a pyrrolidine, piperidine, hexamethyleneimine or morpholine ring, or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1''$ and $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl or $C_{1-3}$-alkoxy, or together with $R_5$ is a trimethylene or tetramethylene group, $R_7$ is hydrogen, chlorine or methyl, n and n' independently of one another are the number 0 or 1 and $A^\ominus$ is a colourless anion.

Preferred distyrylbenzenes of the formula (1), (2) and (5) are those which are symmetrical, i.e. those in which X=X', Y=Y', $Y_1=Y_1'$, $R=R_1'$, $R_2=R_2'$ and n=n'; in which X and X' are not —CON($R_4$)— or —COO— and $X_1$ is not —CONH— or —COO—, which are quaternised, i.e. those in which n and n' are 1, and in which $R_3$ and $R_3'$ are $C_{1-3}$-alkyl.

Preferred distyrylbenzenes of the formulae (1) and (2) which are of interest are those of the formula

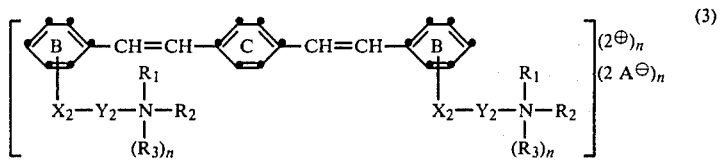

(3)

in which $X_2$ is —COO— or —CONH— in the o-position, oxygen, sulfur, —SO$_2$N(R$_4$) or —OCO—, $Y_2$ is $C_{1-20}$-alkylene, $R_1$ is unsubstituted or substituted $C_{1-8}$-alkyl or $C_{3-4}$-alkenyl, together with $R_2$ is a heterocyclic ring or together with $R_2$ and $R_3$ is a pyridine or picoline ring, $R_2$ is unsubstituted or substituted $C_{1-8}$-alkyl or $C_{3-4}$-alkenyl, together with $R_1$ is a heterocyclic ring or together with $R_1$ and $R_3$ is a pyridine or picoline ring, $R_3$ is hydrogen, unsubstituted or substituted $C_{1-4}$-alkyl or $C_{3-4}$-alkenyl, or together with $R_1$ and $R_2$ is a pyridine or picoline ring, $R_4$ is hydrogen or unsubstituted or substituted $C_{1-6}$-alkyl, n is the number 0 or 1 and $A^\ominus$ is a colourless anion, and the benzene nuclei B and C can also be substituted by non-chromophoric substituents; those of the formula

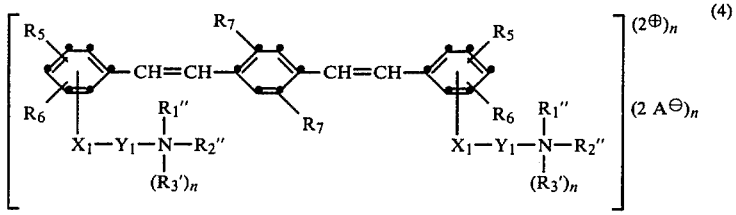

(4)

in which $X_1$ is —COO— or —CONH— in the o-position or a direct bond, oxygen, sulfur, —O—$C_{1-3}$-alkylene—CONH—, —SO$_2$NH—, —O—$C_{1-3}$-alkylene—COO— or —OCO—, $Y_1$ is $C_{1-4}$-alkylene or hydroxypropylene, $R_1''$ and $R_2''$ independently of one another are $C_{1-4}$-alkyl, together are a pyrrolidine, piperidine, hexamethyleneimine or morpholine ring or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1''$ and $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl or $C_{1-3}$-alkoxy, or together with $R_5$ is a trimethylene or tetramethylene group, $R_7$ is hydrogen, chlorine or methyl, n is the number 0 or 1 and $A^\ominus$ is a colourless anion; those of the formula

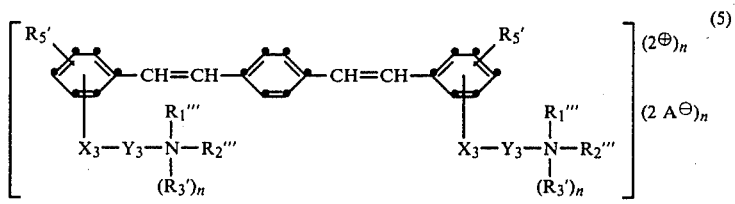

(5)

in which $X_3$ is a direct bond, oxygen, sulfur, —SO$_2$NH or —OCO—, $Y_3$ is $C_{1-4}$-alkylene, $R_1'''$ and $R_2'''$ independently of one another are $C_{1-4}$-alkyl, together are a pyrrolidine, piperidine or morpholine ring, or together with $R_3'$ are a pyridine ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1'''$ and $R_2'''$ is a pyridine ring, $R_5'$ is hydrogen, chlorine, $C_{1-4}$-alkyl or $C_{1-3}$-alkoxy, n is the number 0 or 1 and $A^\ominus$ is a colourless anion, and those of the formula

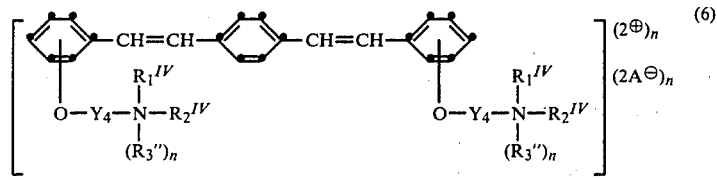

(6)

in which $Y_4$ is $C_{2-4}$-alkylene, $R_1^{IV}$ is $C_{1-3}$-alkyl or together with $R_2^{IV}$ is a pyrrolidine, piperidine, hexamethyleneimine or morpholine ring, $R_2^{IV}$ is $C_{1-3}$-alkyl or together with $R_1^{IV}$ is a pyrrolidine, piperidine, hexamethyleneimine or morpholine ring, $R_3''$ is hydrogen, or $C_{1-3}$-alkyl, n is the number 0 or 1 and $A^\ominus$ is a colourless anion.

Distyrylbenzenes of interest are those of the formula

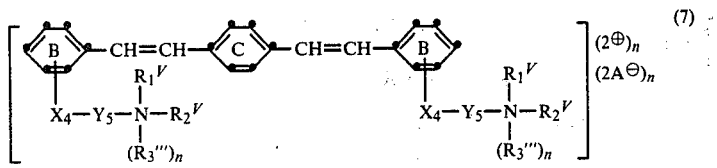

in which $X_4$ is oxygen, sulfur, —OCO—, —COO— or

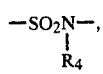

$Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{3-4}$-alkenyl, or together with $R_1^V$ is a heterocyclic ring, $R_3'''$ is hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents; those of the formula

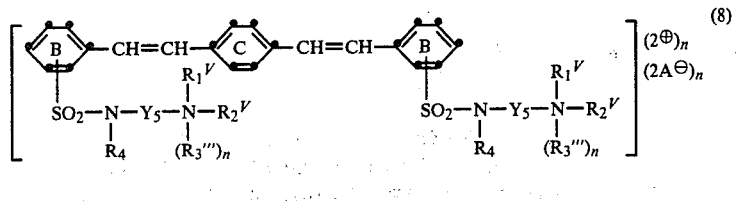

in which $Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{2-4}$-alkenyl, or together with $R_1^V$ is a heterocyclic ring, $R_3'''$ is a hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents, and those of the formula

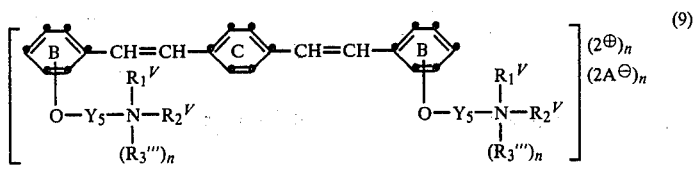

in which $Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{2-4}$-alkenyl, or together with $R_1^V$ is a heterocyclic ring, $R_3'''$ is hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents.

Distyrylbenzenes of particular interest are those of the formula

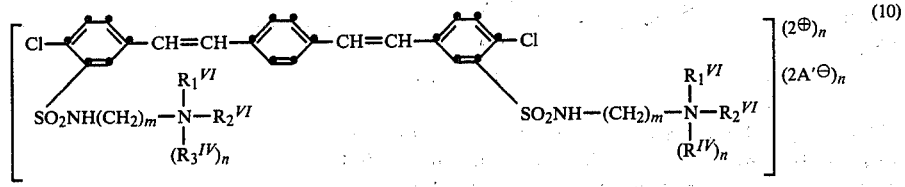

in which $R_1^{VI} = R_2^{VI}$ and both are methyl or ethyl, $R_3^{IV}$ is hydrogen, methyl or ethyl, $A'^\ominus$ is $CH_3OSO_3^\ominus$, $C_2H_5OSO_3^\ominus$ or

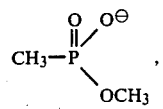

n is the number 0 or 1 and m is the number 2 or 3, those of the formula

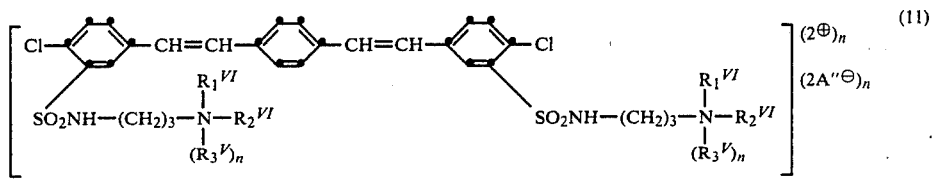

in which $R_1^{VI} = R_2^{VI}$ and both are methyl or ethyl, $R_3^V$ is hydrogen or methyl, $A''^{\ominus}$ is $CH_3OSO_3^{\ominus}$ or

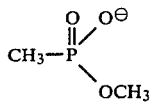

and n is the number 0 or 1, and those of the formulae

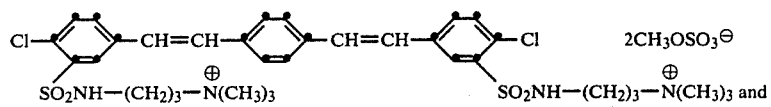

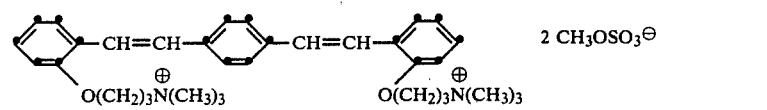

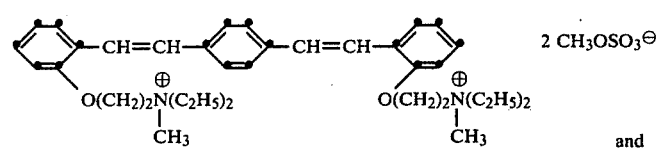

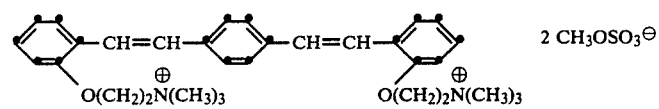

The distyrylbenzenes of the formula (1) in which X is a direct bond, oxygen or sulfur and n and n' are the number 0 are prepared in a manner known per se, by reacting a compond of the formula

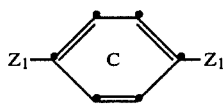

in a molecular ratio of 1:2 with one of the two compounds of the formulae

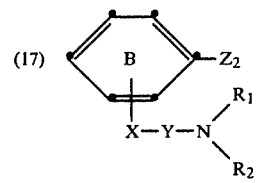 and 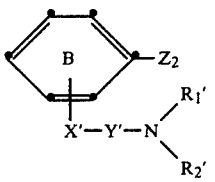

or with a mixture of these two compounds, in the presence of a strong base, in which formulae the benzene nuclei B and C can also be substituted by non-chromophoric substituents, X and X' are a direct bond, oxygen or sulfur and Y, Y', $R_1$, $R_1'$, $R_2$ and $R_2'$ are as defined above and one of the symbols $Z_1$ and $Z_2$ is an OCH group and the other is a grouping of the formula

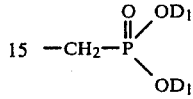 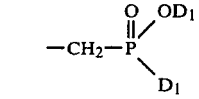

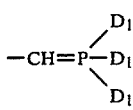

(12)

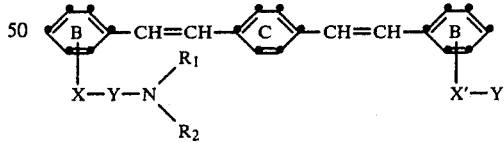

in which $D_1$ is an unsubstituted or substituted alkyl, aryl, cycloalkyl or aralkyl radical, and then quaternising or protonising the resulting compound of the formula in which X, X', Y, Y', $R_1$, $R_1'$, $R_2$ and $R_2'$ are as defined above and the benzene nuclei B and C can also be substituted by non-chromophoric substituents, in a manner known per se, using 1 to 2 mol equivalents of an alkylating agent or, respectively, of an acid of the formula $R_3$—A, in which $R_3$ and A are as defined above. $Z_2$ is preferably an OCH group.

The condensation reaction is advantageously carried out in inert solvents. Examples of such solvents are hydrocarbons, such as toluene and xylene, or alcohols, such as methanol, ethanol, isopropanol and butanol, glycols, glycol ethers, such as 2-methoxyethanol, hexanols, cyclohexanol and cyclooctanol, and also ethers, such as diisopropyl ether, tetrahydrofuran and dioxan, and also dimethylsulfoxide, formamide and N-methylpyrrolidone. Polar organic solvents such as dimethylformamide and dimethylsulfoxide are particularly suitable. Some of the reactions can also be carried out in aqueous solution.

The temperature at which the reaction is carried out can vary within wide limits. It is determined:

(α) by the stability of the solvent used towards the reactants, especially towards the strongly basic alkali metal compounds, (β) by the reactivity of the reactants participating in the condensation reaction and (γ) by the effectiveness of the solvent/base combination as a condensing agent.

In practice, accordingly, in general temperatures between about 10° and 100° C. are suitable. If dimethylformamide is used as the solvent, the preferred temperature range is from 20° to 60° C.

Suitable strongly basic alkali metal compounds are, in particular, the hydroxides, amides and alcoholates (preferably with alcohols containing 1 to 4 carbon atoms) of the alkali metals, and for economic reasons the hydroxides, amides and alcoholates of lithium, sodium and potassium are of predominant interest. In principle, however, and in special cases alkali metal sulfides and alkali metal carbonates, aryl-alkali metal compounds, for example phenyl-lithium, or strongly basic amines (including ammonium bases), for example trialkylammonium hydroxides, can also be used successfully.

The starting materials of the formulae (17) and (18) in which $Z_2$ is an aldehyde group are obtained, for example, by alkylating hydroxybenzaldehydes with dialkylaminoalkyl chlorides in the presence of basic alkali metal compounds or alkaline earth metal compounds, for example sodium alcoholates (see Example 3), potassium carbonate, sodium carbonate, calcium carbonate, magnesium oxide, sodium hydride, potassium hydroxide or sodium hydroxide, in inert organic solvents, such as alcohols or dialkylamides of aliphatic carboxylic acids. Particularly suitable solvents are anhydrous solvents which can also be used in the subsequent stage, i.e. for the preparation of the compounds of the formula (19), for example dimethylformamide, and in this case it is no longer necessary to isolate the compounds of the formulae (17) and (18).

Distyrylbenzenes of the formula

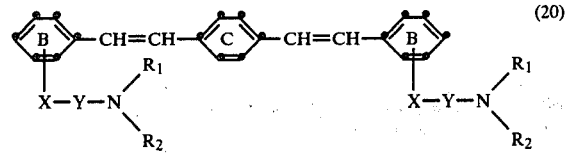

(20)

in which X is —COO— in the o-position, —O—$C_{1-3}$—alkylene—CON($R_4$)—, —O—$C_{1-3}$—alkylene—COO or —SO$_2$N($R_4$)— are prepared in a manner known per se from the corresponding acids (cf., for example, German Offenlegungsschriften 1,923,267 and 2,039,993), by preparing the acid halides in a manner known per se and reacting these halides with a compound of the formula HN($R_4$)—Y—N($R_1$)($R_2$) or HO—Y—N($R_1$)($R_2$).

Distyrylbenzenes of the formula

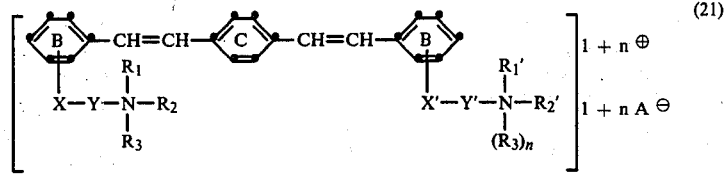

(21)

in which X and X' are —COO— or —CON($R_4$)— in the o-position, a direct bond, oxygen, sulfur, —OCO—, —O—$C_{1-3}$—alkylene—CON($R_4$)—, —O—$C_{1-3}$—alkylene—COO— or —SO$_2$N($R_4$)—, Y and Y' are $C_{1-20}$—alkylene, $R_1$ and $R_1'$ are unsubstituted or substituted $C_{1-8}$-alkyl or $C_{3-4}$-alkenyl, or $R_1$ together with $R_2$, or $R_1'$ together with $R_2'$, is a heterocyclic ring, $R_2$ and $R_2'$ are unsubstituted or substituted $C_{1-8}$-alkyl or $C_{3-4}$-alkenyl, or $R_2$ together with $R_1$, or $R_2'$ together with $R_1'$, is a heterocyclic ring, $R_3$ is hydrogen or unsubstituted or substituted $C_{1-4}$-alkyl or $C_{3-4}$-alkenyl, $A^{\ominus}$ is a colourless anion and n is the number 0 to 1, and the benzene nuclei B and C can also be substituted by non-chromophoric substituents, are prepared by quaternising or protonising one mol equivalent of a distyrylbenzene of the formula (19) in a manner known per se with 1 to 2 mol equivalents of an alkylating agent or of an acid of the formula $R_3$—A, in which $R_3$ and A are as defined above.

Suitable quaternising and protonising agents $R_3$—A are, for example, the following compounds: alkyl halides, such as methyl iodide, ethyl iodide, ethyl bromide or butyl bromide, or benzyl chloride, dialkyl sulfates, such as dimethyl sulfate or diethyl sulfate, sulfonic acid esters, such as methyl toluenesulfonate, ethyl toluenesulfonate, methyl benzenesulfonate or ethyl benzenesulfonate, alkylene oxides, such as ethylene oxide or propylene oxide, or epichlorohydrin, the compounds of the formula

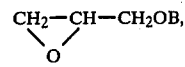

in which B is methyl, ethyl, propyl, butyl or phenyl, and phosphites or phosphonates of the formula

(22)

in which $R_3'''$ is alkyl having 1–4 C atoms, $D_2$ is hydrogen or alkyl which is unsubstituted or substituted by hydroxyl, cyano, alkylcarbonyloxy or alkoxycarbonyl, each having 1 to 4 C atoms in the alkyl moiety, and $D_3$ is alkyl having 1 to 4 C atoms.

The quaternisation of the compounds of the formula (19) with alkyl halides, dialkyl sulfates or sulfonic acid esters to give the compounds of the formula (21) is advantageously carried out in a solvent which is inert towards the alkylating agent. Examples of suitable solvents are hydrocarbons, such as benzene, toluene and xylene, halogenated aliphatic or aromatic hydrocarbons, such as chloroform, ethylene chloride, chlorobenzene and dichlorobenzene, alcohols, such as ethanol and butanol, ethylene glycol and ethylene glycol monomethyl ether, ethers, such as ethylene glycol dimethyl ether and dioxan, or amides, such as dimethylformamide and N-methylpyrrolidone. Sometimes it also proves advantageous to use the quaternising agent as the solvent. Quaternisation with the said alylating agents is advantageously carried out at temperatures between 0° and 180° C. and preferably at 30° to 140° C.

The quaternisation of the compound of the formula (19) with alkylene oxides or epichlorohydrin or its derivatives of the formula

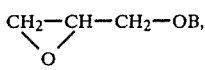

in which B is as defined, to give the compounds of the formula (21), is carried out at the indicated temperatures in an acid medium, advantageously in the presence of an organic acid, such as formic acid, acetic acid, propionic acid or lactic acid; however, inorganic acids, such as sulfuric acid, phosphoric acid or hydrogen halide acids, can also be used for this purpose. These inorganic acids can be used in the concentrated, commercially available form, in the form of dilute aqueous solutions or as a mixture with the said organic solvents, if desired with the addition of water. If the reaction is carried out in the presence of organic acids, these acids are usually used in the concentrated form, if desired as a mixture with the said organic solvents.

Preferred phosphites and phosphonates are, for example, dimethyl phosphite, diethyl phosphite, dimethyl methanephosphonate, diethyl methanephosphonate, methyl ethyl methanephosphonate, methyl propyl methanephosphonate, methyl butyl methanephosphonate, methyl hexyl methanephosphonate, methyl octyl methanephosphonate, methyl decyl methanephosphonate, methyl dodecyl methanephosphonate, dimethyl β-methoxycarbonylethanephosphonate and dimethyl β-cyanoethanephosphonate. The reaction is carried out in water and/or organic solvents, such as methanol, ethanol, propanol, isopropanol, butanol, glycol, glycol methyl ether, glycol dimethyl ether, glycol butyl ether, diglycol methyl ether, methyl ethyl ketone, methyl butyl ketone, dimethylformamide, sulfolane, hydroxypropionitrile, toluene, xylene, benzyl alcohol, phenoxyethanol or benzyloxypropionitrile, at preferably 60° to 190° C. When liquid compounds of the formula (22) are used, the reaction can also be carried out in the absence of an additional solvent.

If protonised compounds of the formula (21), i.e. acid addition salts thereof, are desired, the protonising agents used are in particular mineral acids. In principle, all strong to medium strength organic acids or mineral acids are suitable.

Suitable solvents in which the protonisation can be carried out are, in general, all inert solvents. Preferred solvents are those which dissolve the starting material and from which the end product precipitates immediately. Examples are: aromatic hydrocarbons, such as benzene, toluene and xylene; halogenated hydrocarbons, such as trichloroethane, tetrachloroethylene, chlorobenzene or dichlorobenzene, and also nitro compounds, such as nitromethane, nitropropane or nitrobenzene, alkanols and open or cyclic ethers, such as butanol, dibutyl ether, ethylene glycol, ethylene glycol monomethyl ether, ethylene glycol monoethyl ether, anisole or dioxan; ketones, such as cyclohexanone or methyl ethyl ketone; fatty acid amides, such as dimethylformamide or dimethylacetamide; sulfoxides, such as dimethylsulfoxide, and carboxylic acid esters, such as ethyl acetate or butyl acetate.

Distyrylbenzenes of the formula (1) in which X and X' are the grouping —OCO— and n and n' are the number 1 can be prepared, for example, from the corresponding phenols, by reacting these with a halogenoacyl halide and quaternising the resulting reaction product with a trialkylamine or pyridine of the formula $N(R_1)(R_2)(R_3)$; in the reactants and the reaction product $Y=Y'$, $R_1=R_1'$, $R_2=R_2'$ and $R_3$ are as defined above. The quaternisation is advantageously effected in an inert solvent using at least 2 mols of the amine at 50° to 160° C. and preferably at 80°–130° C.

Distyrylbenzenes of the formula (6) are prepared by reacting a compound of the formula

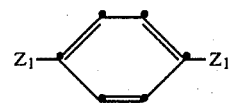

in molecular ratio of 1:2 with a compound of the formula

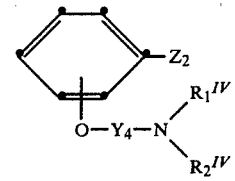

in the presence of a strong base, in which formulae $Y_4$, $R_1^{IV}$ and $R_2^{IV}$ are as defined above and one of the symbols $Z_1$ and $Z_2$ is an OCH group and the other is a grouping of the formula

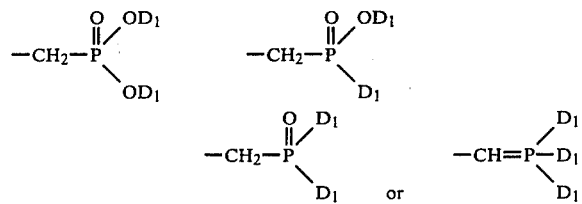

in which $D_1$ is an unsubstituted or substituted alkyl, aryl, cycloalkyl or aralkyl radical, and, if desired, quaternising or protonising the resulting compound of the formula

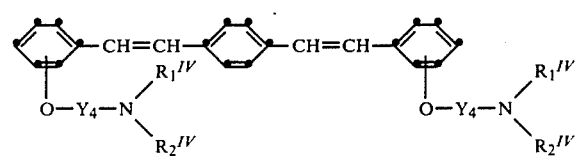

with 2 mol equivalents of an alkylating agent or, respectively, of an acid of the formula $R_3''$—A, in which formulae $Y_4$, $R_1^{IV}$, $R_2^{IV}$, $R_3''$ and A are as defined above.

The novel compounds defined above exhibit a more or less pronounced fluorescence in solution or dispersion. They can be used for the fluorescent brightening of a wide variety of synthetic, regenerated man-made or natural organic materials or substances which contain such organic materials.

The organic materials which are to undergo fluorescent brightening can be in the most diverse states of processing (raw materials, semi-finished goods or finished goods).

The compounds to be used according to the invention are of importance, inter alia, for the treatment of textile organic materials, especially textile fabrics.

Depending on the type of fluorescent brightener compound used, it can prove advantageous to carry out the treatment in a neutral or alkaline or acid bath.

The novel fluorescent brightening agents of the present invention can, for example, also be used for the fluorescent brightening of paper pulps, inter alia in the presence of, for example, cationic retention agents and other additives.

The novel fluorescent brightening agents of the present invention can be employed in the following use forms:
(a) in mixtures with dyes (shading) or pigments (coloured pigments or especially, for example, white pigments) or as an additive to dyebaths,
(b) in mixtures with wetting agents, plasticisers, swelling agents or antioxidants,
(c) in combination with diverse textile finishing processes, for example flameproof finishes, soft-handle finishes, anti-soiling finishes or antistatic finishes or anti-microbial finishes,
(d) incorporation of the fluorescent brightening agents into polymeric carriers (polymerisation, polycondensation or polyaddition products), in dissolved or dispersed form, for use, for example, in coating agents, impregnating agents or binders (solutions, dispersions and emulsions) for textiles, non-wovens, paper and leather,
(e) as additives to a wide variety of industrial products in order to render these more marketable (for example improving the appearance of soaps, detergents, softrinsing agents and textile treatment agents and pigments),
(f) in combination with other fluorescent brightening substances,
(g) in spinning bath preparations, i.e. as additives to spinning baths such as are used for improving the slip for the further processing of synthetic fibres, or from a special bath before stretching the fibre, for example as an after-treatment of wet-spun polyacrylic fibres in the so-called gel state,
(h) for various purposes of a photographic nature, for example for electrophotographic reproduction or supersensitising, and
(i) depending on the substitution, as laser dyes.

If the brightening process is combined with textile treatment or finishing methods, the combined treatment can in many cases advantageously be carried out with the aid of appropriate stable preparations which contain the fluorescent brightener compounds in a concentration such that the desired white effect is achieved.

The amount of the novel fluorescent brightening agents to be used according to the invention, based on the material to undergo fluorescent brightening, can vary within wide limits. A marked and lasting effect can be obtained even with very small amounts and in certain cases, for example, with amounts of 0.0001 percent by weight. However, it is also possible to use amounts of up to about 0.8 percent by weight and, in some cases, of up to about 2 percent by weight. For most practical purposes, it is preferable to use amounts between 0.0005 and 0.5 percent by weight.

For various reasons it is often advantageous not to use the brighteners on their own, i.e. in the pure form, but to use them in the form of a mixture with a wide variety of assistants and extenders.

The novel fluorescent brightening agents are particularly suitable for use as additives to wash liquors or to heavy duty and domestic detergents and laundering after-treatment agents, to which they can be added in various ways. They are advantageously added to wash liquors in the form of their solutions in water or organic solvents, or, in a finely divided form, as aqueous dispersions. They are advantageously added to domestic or heavy duty detergents at any stage of the production process for the detergents. They can be added either in the form of a solution or dispersion in water or other solvents or, without assistants, as a dry brightener powder. For example, the fluorescent brightening agents can be dissolved in the detergent substances or can be mixed, kneaded or ground with the substances and, in this form, admixed with the finished detergent. However, they can also be sprayed in a dissolved or pre-dispersed form onto the finished detergent.

The compounds according to the invention can also be used in a rinsing liquor, such as is customary for merely imparting a soft handle, antistatic properties, anti-soiling effects, fragrances and the like. In particular, they are suitable for use in laundry after-treatment agents which contain cationic softeners.

The novel fluorescent brightening agents are very suitable as fluorescent brighteners for concentrated liquid detergents which contain nonionic surfactants and cationic softeners or surfactants.

The present invention therefore also relates to a detergent, which is preferably in the liquid form and which also contains, in addition to the novel distyrylbenzenes and the customary additives, nonionic surfactants and cationic textile softeners.

Suitable non-ionic surfactants are those which are commercially available, for example the water-soluble products which are obtained by adding an alkylene oxide or an equivalent compound containing a reactive hydrogen onto a hydrophobic compound. The hydrophobic organic products can be heterocyclic compounds and in particular aliphatic compounds or aromatic compounds. Preferred compounds are higher aliphatic alcohols and alkylphenols, but it is also possible to use other compounds, for example carboxylic acids, carboxamides, mercaptans, sulfamides and the like. Preferred nonionic compounds are the adducts of ethylene oxide with higher aliphatic alcohols having 6 to 50 or more C atoms. The amount of ethylene oxide can vary within wide limits, but in general at least 5 mols of ethylene oxide are used per mol of hydrophobic substance. Other lower alkylene oxides, for example propylene oxide and butylene oxide, can be used in place of all or part of the ethylene oxide. Other nonionic compounds which can be used are:
(a) polyoxyalkylene esters of organic acids, such as higher fatty acids, resin acids, tall oil acids and acids of the oxidation products of mineral oil, the esters of which as a rule have 10 to 22 C atoms in the acid moiety and contain about 12 to about 30 mols of ethylene oxide or its equivalent; and (b) alkylene oxide adducts of higher fatty acid amides, in which the fatty acid moiety as a rule has 8 to 22 C atoms and has been subjected to a condensation reaction with 10 to 50 mols of ethylene oxide. The corresponding carboxamides and sulfamides can likewise be used as substantially equivalent compounds.

The nonionic surfactants used in the preparation of liquid, concentrated detergents are preferably oxalkylated higher aliphatic alcohols, the fatty alcohols having at least 6 and preferably at least 8 C atoms. Preferred alcohols are lauryl alcohol, myristyl alcohol, cetyl alcohol, stearyl alcohol and oleyl alcohol, and these are subjected to a condensation reaction with at least 6 mols of ethylene oxide. A typical nonionic product is the adduct of an aliphatic alcohol having 12-13 C atoms with about 6.5 mols of ethylene oxide. After a condensation reaction with ethylene oxide, the corresponding alkylmercaptans can also be used as nonionic surfactants.

The alkoxylated higher aliphatic alcohols are particularly suitable for domestic detergents since they are readily bio-degradable and are readily compatible with cationic surfactants and textile softeners and the other additives.

Suitable cationic textile softeners are, in particular, quaternary derivatives of ammonia and/or of imidazoline with 2 long-chain aliphatic, saturated or unsaturated radicals, for example 1-methyl-1-oleylamidoethyl-2-oleyl-imidazolinium. $X^\ominus$, 1-methyl-1-tallow-amidoethyl-2-tallow-imidazolinium. $X^\ominus$, di-tallow-dimethyl-ammonium .$X^\ominus$ or a compound of the formula

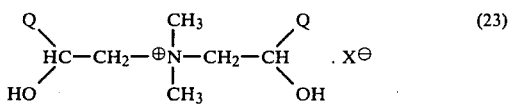  (23)

in which Q is $C_{14\text{-}16}$-alkyl and $X^\ominus$ is a chloride, bromide, methylsulfate, ethylsulfate, methanesulfonate, ethanesulfonate or toluenesulfonate anion.

The quaternary textile softeners which can be used according to the invention, and especially the last-mentioned softeners, impart to the fabric a soft and fluffy handle and, at the same time, make it easy to redampen. These textile softeners are substantive to the fabric and contribute to reducing the static charge and the tendency to crease, so that the fabric can be ironed more easily and is more pleasant to wear.

The liquid medium for the detergents according to the invention is aqueous and can consist of water alone or of water and additional solvents for certain additives. Up to 20%, and preferably up to 15%, of the total amount of solvent can be made up by the additional solvents. Suitable additional solvents are: lower alkanols or a lower diol or polyol, for example ethanol, isopropanol, ethylene-glycol, propylene glycol and glycerol. Etherified polyols, such as diethylene glycol, ethylene glycol dimethyl ether and ethylene glycol monoethyl ether, can also be used as additional solvents.

The liquid detergent according to the invention can contain diverse selected compatible additives, such as soil-suspending agents, or greying inhibitors, for example polyvinyl alcohol and hydroxypropylmethylcellulose; foam inhibitors and preservatives, for example sodium benzoate; UV absorbers and perfumes. These are, of course, so chosen that they are compatible with the main components of the detergent.

The nonionic surfactants are employed in amounts of 10 to 70% by weight and preferably of 60% by weight.

The concentration of the textile softener is 1 to 30% by weight and preferably 2-21% by weight. The aqueous solvent, which is preferably water which can also contain mono-, di- and poly-hydric alcohols and similar solvents, makes up 5 to 60% by weight. The liquid or pulverulent ready-for-use detergent contains the compound according to the invention in amounts of 0.005 to 3% by weight. The content of other assistants preferably makes up less than 5% by weight of the detergent, since the use of larger amounts can influence the properties of liquid detergents. Although the preferred detergent preparation according to the application is a stable, clear liquid, a compatible opacifying agent can be added to produce an opaque appearance.

The detergent according to the invention can be used in soft or suitably hard water at elevated temperature. This detergent can also be used for washing textiles in very hard water at a lower temperature. The hardness of the water can therefore vary between 0 and more than 300 ppm, calculated as calcium carbonate, and the washing temperature can be 4° to 60° C.

The detergent according to the invention dissolves very readily in cold or warm water, cleans thoroughly, eliminates the static charge and makes the laundry soft without rendering it hydrophobic. The preferred detergent is in the form of a clear, stable liquid which retains its activity and uniformity over a prolonged period. For the preparation of clear, liquid detergents, the concentration of the active substances can be varied only within certain limits. Thus, for example, the concentration of the textile softener should not be much higher than 30% if it is desired to obtain a clear, liquid detergent.

The compounds according to the invention are added in amounts of 0.005 to 1% or more, based on the weight of the finished liquid or pulverulent detergent or textile treatment agent. Wash/treatment liquors which contain the indicated amounts of the fluorescent brighteners claimed impart a brilliant appearance in daylight when used to wash textiles made of cellulose fibres, polyamide fibres, resin-finished cellulose fibres, polyester fibres, wool and the like.

The washing treatment is carried out, for example, as follows

The indicated textiles are treated for 1 to 30 minutes at 20° to 100° C. in a wash liquor which contains 0.1 to 10 g/kg of a composite detergent, containing a builder, and 0.01 to 1% based on the weight of the detergent, of the fluorescent brighteners claimed. The liquor ratio can be 1:3 to 1:50. After washing, the textiles are rinsed and dried in the conventional manner.

In the examples, parts are by weight unless stated otherwise and percentages are always by weight. Unless indicated to the contrary, melting points and boiling points are uncorrected and not sharp, especially in the case of the quaternised compounds.

Example 1: 4.2 g of the compound of the formula

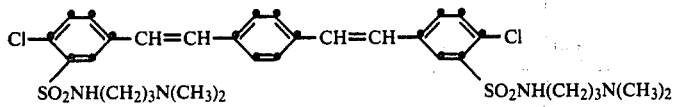
(100)

are suspended in 300 ml of methanol. After adding 6.9 ml of dimethyl sulfate, the mixture is heated to the boil, with stirring, and refluxed for 7 hours. After cooling to room temperature, the product which has crystallised out is filtered off with suction, washed with methanol and dried in vacuo. After extracting with toluene, 4.7 g of the compound of the formula

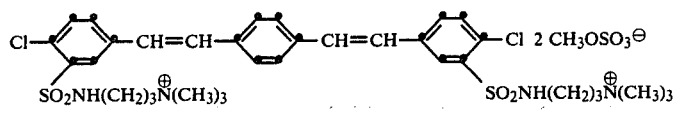
(101)

are obtained in the form of pale yellow crystals with a melting point of 145° 147° C.

The compound of the formula (100) can be obtained as follows 37.3 g of the compound of the formula

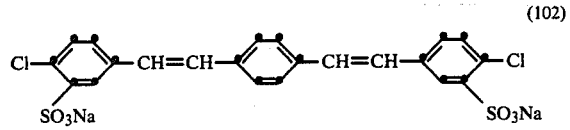
(102)

are suspended in 455 ml of chlorobenzene at room temperature. After adding 1.3 ml of dimethylformamide, 14.5 ml of thionyl chloride are added dropwise in the course for 20 minutes. The mixture is then heated to 95° to 105° C., with stirring, and stirred at this temperature for 4 hours. 120 ml of thionyl chloride and chlorobenzene are then distilled off, the residual mixture is cooled to 5° C. and 21.4 g of calcined sodium carbonate are added slowly. 14.4 g of 3-dimethylamino-1-propylamine in 17 ml of chlorobenzene are added dropwise in the course of 30 minutes to the pale yellow suspension of 5° to 10° C. and the resulting mixture is heated to 106° C. and, after diluting with 300 ml of chlorobenzene, stirred at this temperature for 7 hours. After cooling to 95° C., the mixture is filtered hot, with suction, and the material on the suction filter is washed with chlorobenzene and dried in vacuo. After recrystallising from methanol and then from toluene, 14.7 g of the compound of the formula (100) are obtained in the form of pale yellow crystals with a melting point of 190° to 192° C.

The compound of the formula (102) can be obtained as follows: 18.9 g of tetraethyl p-xylylene-diphosphonate and 25.2 g of the sodium salt of 4-chlorobenzaldehyde-3-sulfonic acid (purity: 96%) are dissolved in 200 ml of dimethylsulfoxide at 40° C., the air being displaced by a stream of nitrogen. 7.2 g of sodium methylate (purity: 97.3%) are then introduced in the course of 20 minutes at 40° to 45° C. and the resulting mixture is stirred for a further 4 hours at 40° to 45° C. 100 ml of demineralised water are then added, with cooling. The product which has crystallised out is filtered off with suction, at 15° C., washed with 100 ml of demineralised water and recrystallised twice, firstly from 2,000 ml of water and then 1,500 ml of water. After drying in vacuo at 85° C., 15.3 g of the compound of the formula (102) are obtained. UV spectrum: $\lambda_{max}$: 363 nm, measured in 1:1 dimethylformamide/water.

Example 2:

3.6 g of the compound of the formula (100) in 25 ml of toluene are refluxed with 5 ml of dimethyl methylphosphonate for 5 hours, with stirring. After cooling to room temperature, the product is filtered off with suction and dried in vacuo. 4.4 g of the compound of the formula

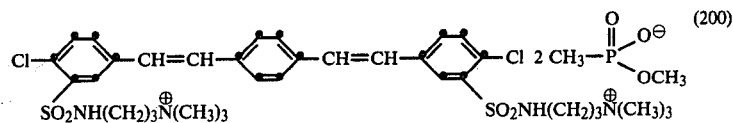
(200)

are thus obtained. Melting point: 201°-209° C.

The following compounds can be prepared by a procedure similar to that described above: the compounds of the formula

| $B_1$ | $B_2$ | $B_3$ | $B_4$ | $B_5$ |
|---|---|---|---|---|
| —SO$_2$NH(CH$_2$)$_3$N(CH$_3$)$_2$ | H | H | H | H |
| H | —SO$_2$NH(CH$_2$)$_2$N(CH$_3$)$_2$ | Cl | H | H |
| H | —SO$_2$NH(CH$_2$)$_3$N(C$_2$H$_5$)$_2$ | Cl | H | H |
| H | —SO$_2$NH(CH$_2$)$_2$N(C$_2$H$_5$)$_2$ | Cl | H | H |
| H | —SO$_2$NH(CH$_2$)$_3$N(CH$_3$)$_2$ | CH$_3$ | H | H |
| H | —SO$_2$NH(CH$_2$)$_3$N(CH$_3$)$_2$ | OCH$_3$ | H | H |
| OCH$_3$ | H | H | —SO$_2$NH(CH$_2$)$_3$N(CH$_3$)$_2$ | H |
| Cl | H | H | —SO$_2$NH(CH$_2$)$_3$N(CH$_3$)$_2$ | H |

-continued $$B_3 \underset{B_2}{\overset{B_4}{\diagdown}} \underset{B_1}{\diagup} - CH=CH - \underset{B_5}{\overset{B_5}{\diagdown}} \diagup - CH=CH - \underset{B_1}{\overset{B_4}{\diagdown}} \underset{B_2}{\diagup} B_3$$

| $B_1$ | $B_2$ | $B_3$ | $B_4$ | $B_5$ |
|---|---|---|---|---|
| —SO$_2$NH(CH$_2$)$_3$N(CH$_3$)$_2$ | H | Cl | H | H |
| CH$_3$ | H | CH$_3$ | —SO$_2$NH(CH$_2$)$_3$N(CH$_3$)$_2$ | H |
| H | —SO$_2$NH(CH$_2$)$_3$N(CH$_3$)$_2$ | CH$_3$ | H | Cl |
| —SO$_2$NH(CH$_2$)$_3$N(CH$_3$)$_2$ | H | H | H | CH$_3$ |
| —CONH(CH$_2$)$_3$N(CH$_3$)$_2$ | H | H | H | H |
| —COO(CH$_2$)$_2$N(C$_2$H$_5$)$_2$ | H | H | H | H | and also the corresponding quaternary compounds of the formula $$\left[ B_3 \underset{B_2}{\overset{B_4}{\diagdown}} \underset{B_1}{\diagup} - CH=CH - \underset{B_5}{\overset{B_5}{\diagdown}} \diagup - CH=CH - \underset{B_1}{\overset{B_4}{\diagdown}} \underset{B_2}{\diagup} B_3 \right]^{(2\oplus)} (2\ A^{\ominus})$$

| $B_1$ | $B_2$ | $B_3$ | $B_4$ | $B_5$ | $A^{\ominus}$ |
|---|---|---|---|---|---|
| —SO$_2$NH(CH$_2$)$_3$N(CH$_3$)$_3$ | H | H | H | H | CH$_3$OSO$_3^{\ominus}$ |
| —SO$_2$NH(CH$_2$)$_3$N(CH$_3$)$_3$ | H | H | H | H | CH$_3$—P(=O)(O$^{\ominus}$)(OCH$_3$) |
| H | —SO$_2$NH(CH$_2$)$_2$N(CH$_3$)$_3$ | Cl | H | H | CH$_3$—P(=O)(O$^{\ominus}$)(OCH$_3$) |
| H | —SO$_2$NH(CH$_2$)$_3$N(C$_2$H$_5$)$_2$CH$_3$ | Cl | H | H | CH$_3$OSO$_3^{\ominus}$ |
| H | —SO$_2$NH(CH$_2$)$_2$N(C$_2$H$_5$)$_2$CH$_3$ | Cl | H | H | CH$_3$—P(=O)(O$^{\ominus}$)(OCH$_3$) |
| H | —SO$_2$NH(CH$_2$)$_3$N(CH$_3$)$_3$ | CH$_3$ | H | H | CH$_3$OSO$_3^{\ominus}$ |
| H | —SO$_2$NH(CH$_2$)$_3$N(CH$_3$)$_3$ | OCH$_3$ | H | H | CH$_3$—P(=O)(O$^{\ominus}$)(OCH$_3$) |
| OCH$_3$ | H | H | —SO$_2$NH(CH$_2$)$_3$N(CH$_3$)$_3$ | H | CH$_3$—P(=O)(O$^{\ominus}$)(OCH$_3$) |
| Cl | H | H | —SO$_2$NH(CH$_2$)$_3$N(CH$_3$)$_3$ | H | CH$_3$—P(=O)(O$^{\ominus}$)(OCH$_3$) |
| —SO$_2$NH(CH$_2$)$_3$N(CH$_3$)$_3$ | H | Cl | H | H | CH$_3$—P(=O)(O$^{\ominus}$)(OCH$_3$) |
| CH$_3$ | H | CH$_3$ | —SO$_2$NH(CH$_2$)$_3$N(CH$_3$)$_3$ | H | CH$_3$—P(=O)(O$^{\ominus}$)(OCH$_3$) |
| H | —SO$_2$NH(CH$_2$)$_3$N(CH$_3$)$_3$ | CH$_3$ | H | Cl | CH$_3$—P(=O)(O$^{\ominus}$)(OCH$_3$) |

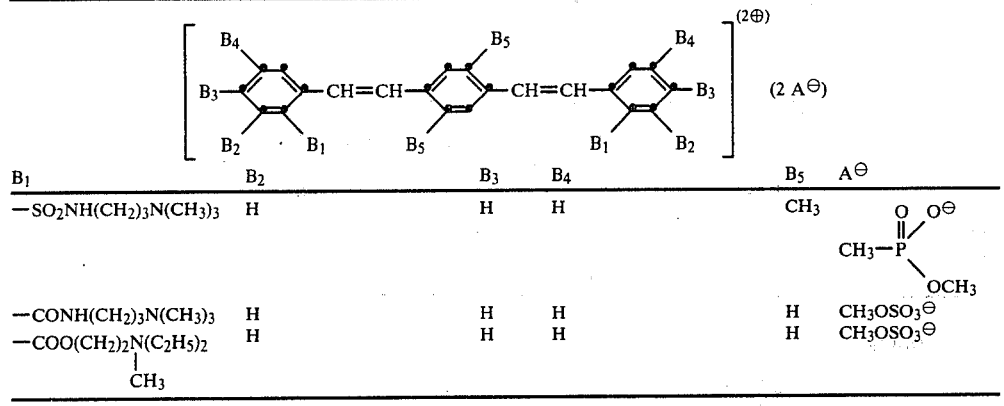

| $B_1$ | $B_2$ | $B_3$ | $B_4$ | $B_5$ | $A^\ominus$ |
|---|---|---|---|---|---|
| —SO$_2$NH(CH$_2$)$_3$N(CH$_3$)$_3$ | H | H | H | CH$_3$ | CH$_3$—P(=O)(O$^\ominus$)OCH$_3$ |
| —CONH(CH$_2$)$_3$N(CH$_3$)$_3$ | H | H | H | H | CH$_3$OSO$_3^\ominus$ |
| —COO(CH$_2$)$_2$N(C$_2$H$_5$)$_2$(CH$_3$) | H | H | H | H | CH$_3$OSO$_3^\ominus$ |

Example 3:

After displacing the air by nitrogen, 88.6 g of a methanolic 30.5% sodium methylate solution are added dropwise, with stirring, to a solution of 75.7 g of 1,4-bis-(diethoxyphosphonomethyl)-benzene and 96.9 g of the compound of the formula

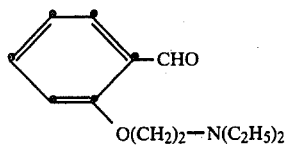

(300)

(purity 96%) in 300 ml of dimethylformamide, at a rate such that the temperature does not rise above 40° C. The temperature is kept at 40°–45° C. for 2 hours, the reaction mixture is cooled with ice-water and 600 ml of water are added. The product which has precipitated is filtered off with suction, washed repeatedly with water and dried in vacuo over calcium chloride. 96.4 g of the compound of the formula

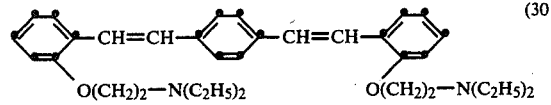

(301)

are obtained in the form of luminous pale yellow crystals with a melting point of 90°–91° C. (after recrystallisation from hexane and isopropanol).

The compound of the formula (300) can be prepared as follows: after displacing the air by nitrogen, 732 g of a methanolic 30.7% sodium methylate solution are added dropwise, with stirring, to a suspension of 244 g of salicylaldehyde and 344 g of 2-diethylamino-ethyl chloride hydrochloride in 2,000 ml of chlorobenzene, whereupon the suspension becomes yellow coloured and thick. The temperature is raised gradually to about 131° C. and during this step the methanol is distilled off. The reaction mixture is kept at this temperature for a further 4 hours and allowed to cool, 500 ml of water are added, the two layers are separated and the organic phase is dried over sodium sulfate. The solvent is then evaporated off under a waterpump vacuum and the residue is subjected to fractional distillation under a high vacuum. After separating off a small amount of first runnings, 327.5 g of a slightly reddish liquid with a boiling point of 105°–118° C./0.06 mbar and a purity of 96% are obtained.

The compounds of the formula

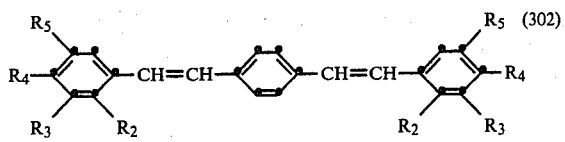

(302)

listed in Table I are obtained analogously by reacting 1,4-bis-(diethoxyphosphonomethyl)-benzene with corresponding aldehydes.

TABLE I

| Formula | $R_2$ | $R_3$ | $R_4$ | $R_5$ | Melting point (°C.) |
|---|---|---|---|---|---|
| (303) | —O(CH$_2$)$_3$—N(CH$_3$)$_2$ | H | H | H | 104° |
| (304) | —O(CH$_2$)$_2$—N(CH$_3$)$_2$ | H | H | H | 116° |
| (305) | —O(CH$_2$)$_2$—N(morpholino, O) | H | H | H | 119° |
| (306) | —O(CH$_2$)$_2$—N(pyrrolidino) | H | H | H | 161° |
| (307) | —O(CH$_2$)$_2$—N(piperidino) | H | H | H | 128° |
| (308) | —O(CH$_2$)$_3$—N(CH$_3$)$_2$ | H | H | —Cl | 110° |
| (309) | —O(CH$_2$)$_3$—N(CH$_3$)$_2$ | H | H | —CH$_3$ | 117° |

TABLE I-continued

| Formula | R2 | R3 | R4 | R5 | Melting point (°C.) |
|---|---|---|---|---|---|
| (310) | (CH2)3—N(CH3)2 | —OCH3 | H | H | 102° |
| (311) | H | —O(CH2)2—N(C2H5)2 | H | H | 86° |
| (312) | H | H | —O(CH2)2—N(C2H5)2 | H | 211° |
| (313) | —OCH2—⟨pyridyl⟩ | H | H | H | 176° |
| (314) | —S(CH2)2—N(CH3)2 | H | H | H | 78° |
| (315) | —CH2N(CH3)2 | H | H | H | 125° |

The aldehyde of the formula

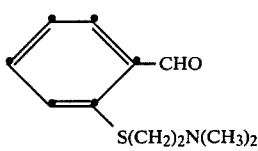

(316)

S(CH2)2N(CH3)2 which is required for the preparation of the compound of the formula (314), can be prepared as follows: after displacing the air by nitrogen, 100 g of approximately 85% pure dimethylamino-ethanethiol hydrochloride are added, with vigorous stirring and cooling, to a mixture of 61.7 g of 88% pure potassium hydroxide in 54.3 g of water and 60 ml of dimethylsulfoxide at a rate such that the temperature does not rise above 20° C. 57.2 g of o-chlorobenzaldehyde are then allowed to run in dropwise and the temperature is kept at 60° C. for 2 hours and then at 80° C. for 2 hours. After cooling to room temperature, 300 ml of methylene chloride and 300 ml of water are added, the whole is mixed thoroughly, the two layers are allowed to separate and the organic phase is dried over sodium sulfate. The solvent is evaporated off and the residue is subjected to fractional distillation under a high vacuum. After separating off the first runnings, 18.6 g of a yellowish liquid with a boiling point of 97°–106° C./0.03 mbar and a purity of 79.3% are obtained.

Example 4:

Example 3 is repeated using a mixture (400) of the two isomeric aldehydes

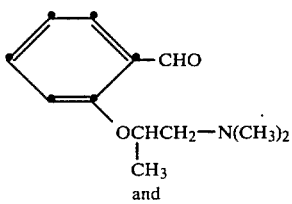

(400a)

OCHCH2—N(CH3)2
|
CH3 and

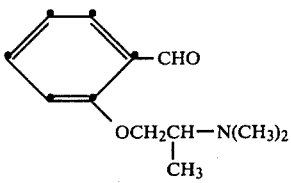

(400b)

OCH2CH—N(CH3)2
|
CH3 in place of an aldehyde which is a single compound. A mixture of isomers (401) is obtained which comprises the two symmetrical compounds of the formulae (401a) and (401b) and the asymmetrical compound of the formula (401c) and has a melting point of 50°–70° C. (after recrystallisation from hexane):

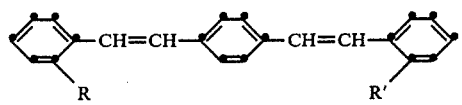

$R = R' = -OCHCH_2-N(CH_3)_2$ (401a)
$\quad\quad\quad\quad |$
$\quad\quad\quad\quad CH_3$ $R = R' = -OCH_2CH-N(CH_3)_2$ (401b)
$\quad\quad\quad\quad\quad |$
$\quad\quad\quad\quad\quad CH_3$ $R = -OCHCH_2-N(CH_3)_2 \quad R' = -OCH_2CH-N(CH_3)_2$ (401c)
$\quad\quad |\quad\quad\quad\quad\quad\quad\quad\quad\quad\quad |$
$\quad\quad CH_3\quad\quad\quad\quad\quad\quad\quad\quad\quad CH_3$ The mixture of the isomers of the aldehydes of the formula (400) is obtained by reacting salicylaldehyde with 2-chloro-1-dimethyl-aminopropane hydrochloride by the method of Example 3, formula (300).

Example 5:

The compounds of the formula

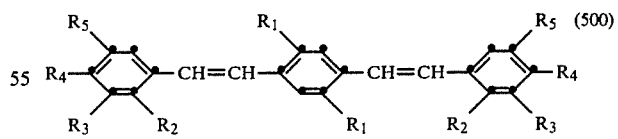

(500)

listed in Table II are obtained by a procedure similar to that described in Example 3.

TABLE II

| Formula | R1 | R2 | R3 | R4 | R5 |
|---|---|---|---|---|---|
| (501) | CH3 | —O(CH2)2—N(C2H5)2 | H | H | H |
| (502) | Cl | —O(CH2)2—N(C2H5)2 | H | H | H |
| (503) | H | —Cl | —O(CH2)2—N(C2H5)2 | H | H |
| (504) | H | —Cl | H | —O(CH2)2—N(C2H5)2 | H |
| (505) | H | —O(CH2)2—N(C2H5)2 | Cl | H | Cl |

TABLE II-continued

| Formula | R1 | R2 | R3 | R4 | R5 |
|---|---|---|---|---|---|
| (506) | H | —O(CH$_2$)$_2$—N(C$_2$H$_5$)$_2$ | H | —(CH$_2$)$_3$— | |
| (507) | H | —O(CH$_2$)$_2$—N(C$_2$H$_5$)$_2$ | H | —(CH$_2$)$_4$— | |
| (508) | H | H | H | —O(CH$_2$)$_3$—N(CH$_3$)$_2$ | H |
| (509) | H | H | H | —O(CH$_2$)$_2$—N(CH$_3$)$_2$ | H |
| (510) | H | —O(CH$_2$)$_2$—N(C$_2$H$_5$)$_2$ | —CH$_2$CH=CH$_2$ | H | H |
| (511) | H | CH$_3$ | H | —O(CH$_2$)$_2$—N(C$_2$H$_5$)$_2$ | —CH(CH$_3$)$_2$ |
| (512) | H | —O(CH$_2$)$_2$—N(C$_2$H$_5$)$_2$ | CH$_3$ | H | CH$_3$ |
| (513) | H | —O(CH$_2$)$_2$—N(C$_2$H$_5$)$_2$ | H | CH$_3$ | Cl |
| (514) | H | —OCH$_2$C(O)NH(CH$_2$)$_3$—N(CH$_3$)$_2$ | H | H | H |
| (515) | H | —OCH$_2$CO(CH$_2$)$_2$—N(CH$_3$)$_2$ | H | H | H |

The compounds of the formulae (514) and (515) are obtained by reacting

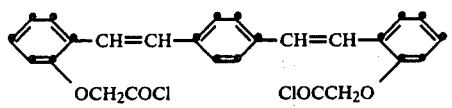

(prepared by the method of German Offenlegungsschrift 2,209,128) with 3-dimethylamino-1-propylamine and, respectively, 2-dimethylaminoethanol, analogously to Example 1, formula (100).

Example 6:

2.5 ml of dimethyl sulfate are added dropwise at about 70° C., with stirring, to a solution of 4.85 g of the compound of the formula (303) in 50 ml of methyl ethyl ketone. The reaction mixture is refluxed for a further 1 hour and allowed to cool and the product which has precipitated is filtered off with suction and washed repeatedly with methyl ethyl ketone. After drying in vacuo at 100° C., 7.2 g (96% of theory) of the compound of the formula

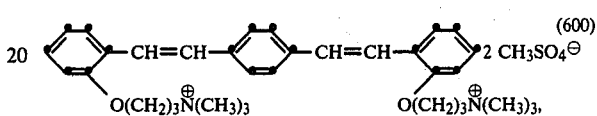

which contains about ½ mol of water of crystallisation, are obtained in the form of luminous pale yellow crystals with a melting point of 254° C. (unsharp).

It is also possible to use chlorobenzene as the solvent, in place of methyl ethyl ketone.

When this example is repeated, reducing the amount of dimethyl sulfate employed from 2.5 ml to 1.0 ml, this yields a mixture of the symmetrical compound of the formula (600) and the asymmetrical compound of the formula

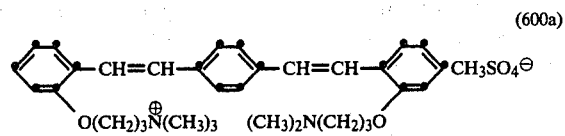

The fluorescent brightening agents of the formula

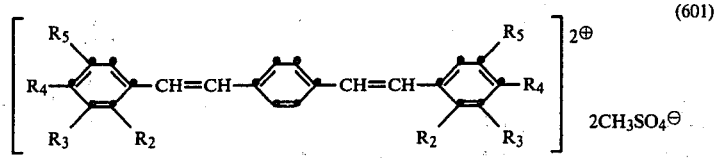

listed in Table III below are obtained in an analogous manner from the compound of the formula (301) and the compounds described in Table I.

TABLE III

| Formula | R2 | R3 | R4 | R5 | Melting point (°C.) |
|---|---|---|---|---|---|
| (602) | —O(CH$_2$)$_2$—N(C$_2$H$_5$)$_2$ / CH$_3$ | H | H | H | 223° |
| (603) | —O(CH$_2$)$_2$—N(CH$_3$)$_3$ | H | H | H | 259° |
| (604) | —O(CH$_2$)$_2$—N(CH$_3$)(morpholino) | H | H | H | 189° |
| (605) | —O(CH$_2$)$_2$—N(CH$_3$)(aziridinyl) | H | H | H | 175° |

TABLE III-continued

| Formula | R₂ | R₃ | R₄ | R₅ | Melting point (°C.) |
|---|---|---|---|---|---|
| (606) | −O(CH₂)₂−N(morpholine with CH₃) | H | H | H | 181° |
| (607) | −O(CH₂)₃−N(CH₃)₃ | H | H | −Cl | 284° |
| (608) | −O(CH₂)₃−N(CH₃)₃ | H | H | −CH₃ | 233° |
| (609) | −O(CH₂)₃−N(CH₃)₃ | −OCH₃ | H | H | 174° |
| (610) | H | −O(CH₂)₂−N(C₂H₅)₂ with CH₃ | H | H | 169° |
| (611) | H | H | −O(CH₂)₂−N(C₂H₅)₂ with CH₃ | H | 191° |
| (612) | −OCH₂−(N-methylpyrrole) | H | H | H | 164° |
| (613) | −S(CH₂)₂−N(CH₃)₃ | H | H | H | 225° |
| (614) | −CH₂N(CH₃)₃ | H | H | H | 278° (with decomposition) |

For the preparation of the compound of the formula (611), 100 ml of 1,2-dichloroethane are used in place of methyl ethyl ketone. For the preparation of the compounds of the formulae (605) and (612), a little dimethylformamide is also added in order to dissolve the starting materials completely.

Example 7:

The mixture of isomers of the formula (401) is quaternised by the method of Example 5. A mixture of the isomers of the formula (700) is obtained which comprises the two symmetrical compounds (700a) and (700b) and the asymmetrical compound of the formula (700c)

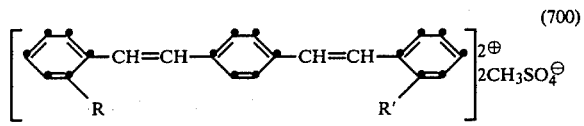
(700)

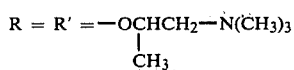
R = R' = −OCHCH₂−N(CH₃)₃
          |
          CH₃
(700a)

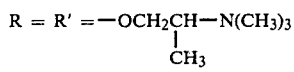
R = R' = −OCH₂CH−N(CH₃)₃
            |
            CH₃
(700b)

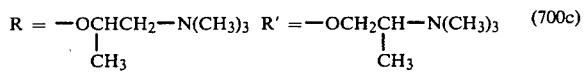
R = −OCHCH₂−N(CH₃)₃    R' = −OCH₂CH−N(CH₃)₃
     |                         |
     CH₃                       CH₃
(700c)

with a melting point of 240° C. (unsharp) and contains about ½ mol of water of crystallisation.

Example 8:

5.5 g of trimethylamine are passed into a solution of 4.7 g of the compound of the formula

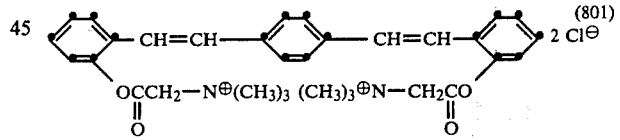
(800)

in 50 ml of chlorobenzene, at 90° C., in the course of 10 minutes, with stirring. The mixture is stirred for a further 15 minutes at this temperature and the product which has precipitated is filtered off with suction at about 60° C., washed repeatedly with methyl ethyl ketone and dried in vacuo at 100° C. 5.0 g of the compound of the formula (801)

with a melting point of 235°–238° C. are obtained.

When this example is repeated using 3.2 ml of pyridine in place of trimethylamine and 50 ml of methyl ethyl ketone as the solvent and the reaction is carried out under reflux (for 1 hour), 3.8 g of a compound of the formula

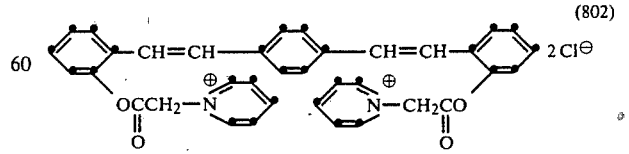
(802)

with a melting point of 227°–235° C. (with decomposition) are obtained.

The compound of the formula (800), which is required as the starting material, is obtained as follows:

after displacing the air by nitrogen, 126.6 g of a methanolic 30.7% sodium methylate solution are added dropwise, with stirring, to a solution of 21.5 g of terephthalaldehyde and 158.2 g of the compound of the formula

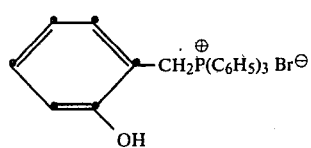
(803)

in 500 ml of dimethylformamide at a rate such that the temperature does not rise above 40° C. The temperature is kept at 40°-45° C. for 2 hours, the reaction mixture is allowed to cool and 150 ml of water are added. The resulting mixture is neutralised to pH 8 by passing in carbon dioxide until the mixture is saturated, or by adding solid carbon dioxide, and the yellowish coloured reaction product precipitates. This is filtered off with suction, washed repeatedly with water, dried in vacuo and recrystallised from methyl ethyl ketone. 13.8 g of the compound of the formula

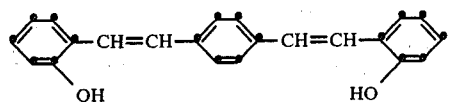

with a melting point of 275°-280° C. are obtained.

12.6 g of the compound of the formula (804) are stirred in 40 ml of chloroacetyl chloride overnight, under reflux, and finally everything dissolves. 40 ml of cyclohexane are added, the mixture is cooled and the product which has precipitated is filtered off with suction, washed repeatedly with cyclohexane and dried in vacuo at 80° C. After recrystallisation from nonane, 11.6 g of the compound of the formula (800) are obtained in the form of pale yellow crystals with a melting point of 146°-149° C.

Example 9:

The compounds of the formula

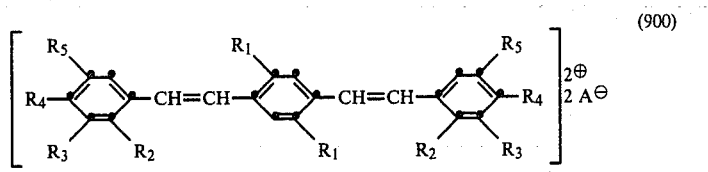
(900)

listed in Table IV are obtained in a manner similar to that described in Examples 5 or 7.

TABLE IV

| Formula | $R_1$ | $R_2$ | $R_3$ | $R_4$ | $R_5$ | A |
|---|---|---|---|---|---|---|
| (901) | $CH_3$ | $-O(CH_2)_2-N(C_2H_5)_2$ $\mid$ $CH_3$ | H | H | H | $CH_3OSO_3$ |
| (902) | Cl | $-O(CH_2)_2-N(C_2H_5)_2$ $\mid$ $CH_3$ | H | H | H | " |
| (903) | H | $-Cl$ | $CH_3$ $\mid$ $-O(CH_2)_2-N(C_2H_5)_2$ | H | H | " |
| (904) | H | $-Cl$ | H | $CH_3$ $\mid$ $-O(CH_2)_2-N(C_2H_5)_2$ | H | " |
| (905) | H | $CH_3$ $\mid$ $-O(CH_2)_2-N(C_2H_5)_2$ | $-Cl$ | H | $-Cl$ | " |
| (906) | H | $CH_3$ $\mid$ $-O(CH_2)_2-N(C_2H_5)_2$ | H | $-(CH_2)_3-$ | | " |
| (907) | H | $CH_3$ $\mid$ $-O(CH_2)_2-N(C_2H_5)_2$ | H | $-(CH_2)_4-$ | | " |
| (908) | H | H | H | $-O(CH_2)_3-N(CH_3)_3$ | H | " |
| (909) | H | H | H | $-O(CH_2)_2-N(CH_3)_3$ | H | " |
| (910) | H | $CH_3$ $\mid$ $-O(CH_2)_2-N(C_2H_5)_2$ | $-CH_2CH=CH_2$ | H | H | " |
| (911) | H | $-CH_3$ | H | $CH_3$ $\mid$ $-O(CH_2)_2-N(C_2H_5)_2$ | $CH_3$ $\mid$ $-CH$ $\diagdown$ $CH_3$ | " |
| (912) | H | $CH_3$ $\mid$ $-O(CH_2)_2-N(C_2H_5)_2$ | $-CH_3$ | H | $-CH_3$ | " |
| (913) | H | $CH_3$ $\mid$ $-O(CH_2)_2-N(C_2H_5)_2$ | H | $CH_3$ | Cl | " |
| (914) | H | $-OCH_2CHCH_2N(CH_3)_2$ $\mid$ $OH$ | H | H | H | " |

TABLE IV-continued

| Formula | $R_1$ | $R_2$ | $R_3$ | $R_4$ | $R_5$ | A |
|---|---|---|---|---|---|---|
| (915) | H | H | H | —O(CH$_2$)$_2$—N(C$_2$H$_5$)$_2$<br>\|<br>CH$_3$ | H | CH$_3$\\O<br>\\\|\|<br>PO<br>/<br>CH$_3$O |
| (916) | H | —O(CH$_2$)$_2$—N(C$_2$H$_5$)$_3$ | H | H | H | Br |
| (917) | H | —O(CH$_2$)$_2$—N(C$_2$H$_5$)$_2$<br>\|<br>CH$_2$C$_6$H$_5$ | H | H | H | Cl |
| (918) | H | H | H | —O(CH$_2$)$_2$—N(C$_2$H$_5$)$_2$<br>\|<br>CH$_2$COOCH$_3$ | H | Cl |
| (919) | H | —O(CH$_2$)$_2$—N(C$_2$H$_5$)$_2$<br>\|<br>CH$_3$ | H | H | H | CH$_3$—⟨furan⟩—SO$_3$ |
| (920) | H | H | H | —O(CH$_2$)$_2$—N(C$_2$H$_5$)$_2$<br>\|<br>CH$_2$CN | H | Cl |
| (921) | H | H | H | —O(CH$_2$)$_3$—N(CH$_3$)$_2$<br>\|<br>C$_2$H$_5$ | H | C$_2$H$_5$OSO$_3$ |
| (922) | H | H | H | —CH$_2$N(CH$_3$)$_3$ | H | Cl |
| (923) | H | —OCH$_2$C(O)NH(CH$_2$)$_3$N(CH$_3$)$_3$ | H | H | H | CH$_3$OSO$_3$ |
| (924) | H | —OCH$_2$C(O)O(CH$_2$)$_2$N(CH$_3$)$_3$ | H | H | H | CH$_3$OSO$_3$ |
| (925) | H | —O(CH$_2$)$_3$—N(CH$_3$)$_2$<br>\|<br>CH$_2$CH=CH$_2$ | H | H | H | Cl |
| (926) | H | —O(CH$_2$)$_3$—N(CH$_3$)$_2$<br>\|<br>CH$_2$CH$_2$OH | H | H | H | CH$_3$COO |
| (927) | H | —O(CH$_3$)$_3$—N(CH$_3$)$_2$<br>\|<br>CH$_2$CHCH$_3$<br>\|<br>OH | H | H | H | HCOO |

Example 10:

Using a liquor ratio of 1:20, a bleached cotton fabric is treated on a dyeing apparatus with an aqueous liquor which contains 0.1% of the fluorescent brightener of the formula (101), (200), (600), (602) to (606) or (700), based on the weight of the cotton, and 5 g/l of sodium sulfate.

The application is carried out in accordance with the following temperature programme: 15 minutes at 20°–50° C. and 15 minutes at 50° C.

The cotton fabric is then rinsed for 20 seconds in running softened water and dried at 70° C. in a drying cabinet. The cotton fabric treated in this way has a good white effect.

Example 11:

A bleached cotton fabric is padded at room temperature with an aqueous liquor which contains 1 g/l of the fluorescent brightener of the formula (101) or (200). The liquor pick-up is 75%.

The fabric is then dried for 30 seconds at 130° C. on a thermofixing apparatus.

The cotton fabric treated in this way has a good white effect.

Example 12

Using a liquor ratio of 1:20, a polyacrylonitrile fabric (Orlon 75) is treated on a dyeing apparatus with an aqueous liquor which contains 0.1% of the fluorescent brightener of the formula (101), (200), (301), (303) to (307), (401), (600), (602) to (606) or (700), based on the weight of goods, 1 g/l of an adduct of 35 mols of ethylene oxide with 1 mol of stearyl alcohol and 1.5 ml/l of 85% formic acid.

The application is carried out in accordance with the following temperature programme: 30 minutes at 40°–97° C., 30 minutes at 97° C. and 15 minutes at 97°–40° C.

The polyacrylonitrile fabric is then rinsed for 20 seconds in running softened water and dried at 70° C. in a drying cabinet. The fabric treated in this way has a good white effect.

Example 13:

Using a liquor ratio of 1:20, a polyacrylonitrile fabric (Courtelle ®) is treated on a dyeing apparatus with an aqueous liquor which contains 0.1% of the fluorescent brightener of the formula (301), (303) to (307), (401), (600), (602) to (606) or (700), based on the weight of fabric, 1 g/l of oxalic acid, 0.25 g/l of sodium hexametaphosphate and 0.125 g/l of sodium metabisulfite.

The application is carried out in accordance with the following temperature programme: 30 minutes at 40°–100° C., 30 minutes at 100° C. and 15 minutes at 100°–40° C. The polyacrylonitrile fabric is then rinsed for 30 seconds in running softened water, centrifuged and dried with a hot iron at 150° C. The fabric treated in this way has a good white effect.

Example 14:

Using a liquor ratio of 1:20, a bleached cotton fabric is treated for 15 minutes in a warm, aqueous soft-rinse liquor which is at 30° C. and contains, per liter, 0.2 g of quaternary dimethyldistearylammonium chloride and 0.01 g of the fluorescent brightener of the formula (101), (200), (600) or (602).

The cotton fabric is then rinsed for 5 seconds in running drinking water and dried at 70° C. in a drying cabinet. The cotton fabric treated in this way has a good white effect.

Example 15:

Using a liquor ratio of 1:20, a bleached cotton fabric is washed for 15 minutes in a warm aqueous liquor which is at 40° C. and contains, per liter, 0.5 g of an adduct of 10 mols of ethylene oxide with 1 mol of stearyl alcohol and 0.01 g of the fluorescent brightener of the formula (101), (200), (600) or (602) to (606).

The cotton fabric is then rinsed for 20 seconds in running drinking water and dried at 70° C. in a drying cabinet. The cotton fabric treated in this way has a good white effect.

When the above procedure is repeated, except that 0.2 g/l of active chlorine in the form of sodium hypochlorite is also added to the liquor described above, good white effects are again obtained with the fluorescent brightener of the formula (600).

Example 16:

Using a liquor ratio of 1:20, a piece of polyamide textured tricot is washed for 15 minutes in a warm aqueous liquor which is at 40° C. and contains, per liter, 0.5 g of an adduct of 10 mols of ethylene oxide with 1 mol of stearyl alcohol and 0.01 g of the fluorescent brightener of the formula (101) or (200).

The polyamide tricot is then rinsed for 20 seconds in running drinking water and dried at 70° C. in a drying cabinet. The polyamide tricot treated in this way has a good white effect.

Example 17:

A polyamide-6 fabric is padded with a liquor which contains 1 g/l of the fluorescent brightener of the formula (301), (303) to (306), (313) or (401), 1 g/l of an adduct of 1 mol of stearyl alcohol with 35 mols of ethylene oxide, 1 g/l of an adduct of 1 mol of p-tert.-octylphenol with 8 mols of ethylene oxide, 90 ml of ethanol (95%) and 0.5 g/l of sodium phosphate buffer. The fabric is squeezed out to a liquor pick-up of 85%. The fabric treated in this way is now put into a dyeing apparatus which contains water in an amount such that the liquor ratio is 1:25. The application is now carried out in accordance with the following temperature programme: 10 minutes at 50°-100° C., 20 minutes at 100° C. and 5 minutes at 100°-50° C.

The fabric is then rinsed in cold softened water, centrifuged and dried with a hot iron at 180° C. The polyamide-6 fabric treated in this way has a good white effect.

Example 18:

A polyamide-6 fabric is padded with a liquor which contains 1 g/l of the fluorescent brightener of the formula (600), (602) to (606) or (700), 1 g/l of an adduct of 1 mol of stearyl alcohol with 35 mols of ethylene oxide, 1 g/l of an adduct of 1 mol of p-tert.-octylphenol with 8 mols of ethylene oxide, 90 ml of ethanol (95%) and 2 g/l of sodium tripolyphosphate. The fabric is squeezed out to a liquor pick-up of 85%. The fabric treated in this way is now put into a dyeing apparatus which contains water in an amount such that the liquor ratio is 1:25. The application is now carried out in accordance with the following temperature programme: 10 minutes at 30°-60° C. and 20 minutes at 60° C.

The fabric is then rinsed in cold softened water, centrifuged and dried with a hot iron at 180° C. The polyamide-6 fabric treated in this way has a good white effect.

EXAMPLE 19:

A bleached cotton fabric is padded with a liquor which contains 1 g/l of the fluorescent brightener of the formula (600), (602) to (606) or (700), 1 g/l of an adduct of 1 mol of stearyl alcohol with 35 mols of ethylene oxide, 1 g/l of an adduct of 1 mol of p-tert.-octylphenol with 8 mols of ethylene oxide, 90 ml of ethanol (95%) and 2 g/l of sodium tripolyphosphate. The fabric is squeezed out to a liquor pick-up of 75%. The fabric treated in this way is now put into a drying apparatus which contains water in an amount such that the liquor ratio is 1:25. The application is now carried out in accordance with the following temperature programme: 10 minutes at 30°-70° C. and 20 minutes at 70° C.

The fabric is then rinsed in cold softened water, centrifuged and dried with a hot iron at 155° C. The cotton fabric treated in this way has a good white effect.

Example 20:

5 g of fibrous material (consisting of bleached sulfite cellulose and bleached beech cellulose, 1:1) in 50 ml of water are mixed for 15 minutes in a mixer with 150 ml of fluorescent brightener solution containing 4 mg, corresponding to a concentration of 0.08%, of the fluorescent brightener of the formula (100), (200) or (600). 1.5% by weight of size, for example Bewoidleim ®, and 2.5% by weight of aluminium sulfate (based on the weight of dried fiber) are then added and the mixture is diluted to 1,000 ml with water of about 10° German hardness. This fibre suspension is used to form a sheet of paper and this has a good white effect.

Example 21:

5 g of fibrous material (consisting of bleached sulfite cellulose and bleached beech cellulose, 1:1) in 150 ml of water containing 5 mg of a cationic polyetheramine are mixed for 15 minutes in a mixer with 50 ml of fluorescent brightener solution containing 4 mg, corresponding to a concentration of 0.08%, of the fluorescent brightener of the formula (200) or (600). 1.5% by weight of size, for example Bewoidleim ®, 2.5% by weight of aluminium sulfate and 0.1% of a cationic polyether-amine (based on the weight of dry fibre) are then added and the mixture is diluted to 1,000 ml with water to about 10° German hardness. This fibre suspension is used to form a sheet of paper and this has a good white effect.

Example 22:

5 g of fibrous material (consisting of bleached sulfite cellulose and bleached beech cellulose, 1:1) in 150 ml of water containing 5 mg of a polyethyleneimine are mixed for 15 minutes in a mixer with 50 ml of fluorescent brightener solution containing 4 mg, corresponding to a concentration of 0.08%, of the fluorescent brightener of the formula (200) or (600). 1.5% by weight of size, for example Bewoildeim ®, 2.5% by weight of aluminium sulfate and 0.1% of a polyethyleneimine (based on the weight of dry fibre) are then added and the mixture is diluted to 1,000 ml with water of about 10° German hardness. This fibre suspension is used to form a sheet of paper and this has a good white effect.

Example 23:

A concentrated liquid detergent is prepared by mixing the following components:

| | % by weight |
|---|---|
| ethoxylated alcohols ($C_{12}$–$C_{13}$ alcohol with 6.5 mols of ethylene oxide) | 60.0 |
| 1-methyl-1-oleylamidoethyl-2-oleyl-imidazolinium methosulfate | 26.7 |
| the compound of the formula (101), (200), (600), (602) to (606) or (700) | 0.3 |
| water | 12.0 |
| conventional additives | 1.0 |

2 kg of bleached cotton fabric are washed for 10 minutes at 50° C. in 60 liters of water of 100 ppm hardness, which contains 50 to 60 g of the above detergent. After rinsing and drying, the fabric has a powerful white effect and a soft handle.

Similar results were obtained using, in place of the above detergent, a liquid detergent of the following composition:

| | % by weight |
|---|---|
| ethoxylated alcohols ($C_{12}$–$C_{13}$ alcohol with 6.5 mols of ethylene oxide) | 55.0 |
| 1-methyl-1-tallow-amidoethyl-2-tallow-imidazolinium methosulfate | 26.0 |
| the compound of the formula (101), (200), (600), (602) to (606) or (700) | 0.3 |
| water | 13.0 |
| isopropanol | 5.0 |
| conventional additives | 0.7, | or another liquid detergent containing nonionic surfactants and cationic substances, for example "Perwoll ® liquid" or Samtess ®, which are available commercially, and to which the fluorescent brighteners according to the invention have been admixed.

Example 24:

A liquid detergent is prepared by mixing the following components:

| | % by weight |
|---|---|
| ethoxylated alcohols ($C_{14}$–$C_{15}$ alcohol with 7 mols of ethylene oxide) | 12.0 |
| ethoxylated alcohols ($C_{12}$–$C_{13}$ alcohol with 6.5 mols of ethylene oxide) | 12.0 |
| non-cured di-tallow-dimethyl-ammonium chloride | 6.4 |
| ethanol | 15.0 |
| sodium bicarbonate | 0.25 |
| the compound of the formula (600), (602) to (606) or (700) | 0.41 |
| conventional additives | 0.41 |
| water | 53.53 |

A cotton fabric treated as described in Example 23 has a powerful white effect and a soft handle.

Example 25:

An intimate mixture of 100 parts of polyvinyl chloride, 3 parts of stabiliser (Advastat BD 100 ®; Ba/Cd complex), 2 parts of titanium dioxide, 59 parts of dioctyl phthalate and 0.01 to 0.2 part of a compound of the formula (301), (303) to (306) or (401) is rolled out on a calender at 150° to 155° C. to give a film. The opaque polyvinyl chloride film thus obtained has a substantially higher whiteness than a film which does not contain the fluorescent brightening agent.

What is claimed is:

1. A distyrylbenzene of the formula

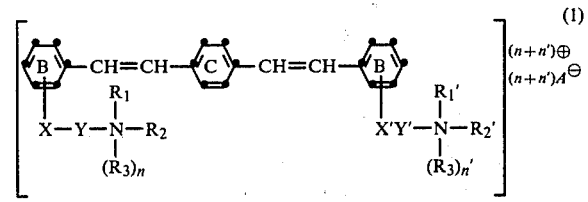

in which X and X' independently of one another are —COO— or —CON($R_4$)— in the o-position, a direct bond, oxygen, sulfur, —O—$C_{1-3}$-alkylene—CON($R_4$)—, —$SO_2$N($R_4$)—, —O—$C_{1-3}$-alkylene—COO— or —OCO—, Y and Y' independently of one another are $C_{1-20}$-alkylene, $R_1$ and $R_1'$ independently of one another are unsubstituted or substituted $C_{1-8}$-alkyl or $C_{3-4}$-alkenyl, or $R_1$ together with $R_2$, or $R_1'$ together with $R_2'$, is a heterocyclic ring, $R_2$ and $R_2'$ independently of one another are unsubstituted or substituted $C_{1-8}$-alkyl or $C_{3-4}$-alkenyl, or $R_2$ together with $R_1$, or $R_2'$ together with $R_1'$, is a heterocyclic ring, or $R_1$ and $R_2$, or $R_1'$ and $R_2'$, together with $R_3$ are a pyridine or picoline ring, $R_3$ is hydrogen, unsubstituted or substituted $C_{1-4}$-alkyl or $C_{3-4}$-alkenyl, or together with $R_1$ and $R_2$ or with $R_1'$ and $R_2'$ is a pyridine or picoline ring, $R_4$ is hydrogen or unsubstituted or substituted $C_{1-6}$-alkyl, $A^\ominus$ is a colourless anion and n and n' independently of one another are the number 0 or 1, and the benzene nuclei B and C can also be substituted by non-chromophoric substituents.

2. A distyrylbenzene according to claim 1, of the formula

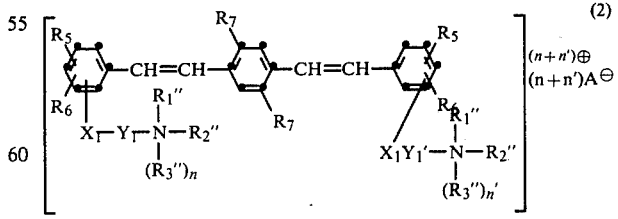

in which $X_1$ is —COO— or —CONH— in the o-position, a direct bond, oxygen, sulfur, —O—$C_{1-3}$-alkylene—CONH—, —$SO_2$NH—, —O—$C_{1-3}$-alkylene—COO— or —OCO—, $Y_1$ and $Y_1'$ independently of one another are $C_{1-4}$-alkylene or hydroxypropylene, $R_1''$ and $R_2''$ independently of one another are $C_{1-4}$-alkyl or together are a pyrrolidine, piperidine, hexamethyleneimine or morpholine ring, or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1''$ and $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl or $C_{1-3}$-alkoxy, or together with $R_5$ is a trimethylene or tetramethylene group, $R_7$ is hydrogen, chlorine or methyl, n and n' independently of one another are the number 0 or 1 and $A^\ominus$ is a colourless anion.

3. A distyrylbenzene according to claim 1, of the formula

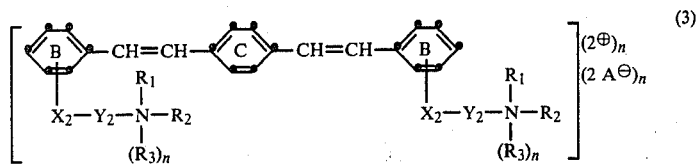

(3)

in which $X_2$ is —COO— or —CONH— in the o-position, oxygen, sulfur, —SO$_2$N(R$_4$)— or —OCO—, $Y_2$ is $C_{1-20}$-alkylene, $R_1$ is unsubstituted or substituted $C_{1-8}$-alkyl or $C_{3-4}$-alkenyl, together with $R_2$ is a heterocyclic ring or together with $R_2$ and $R_3$ is a pyridine or picoline ring, $R_2$ is unsubstituted or substituted $C_{1-8}$-alkyl or $C_{3-4}$-alkenyl, together with $R_1$ is a heterocyclic ring or together with $R_1$ and $R_3$ is a pyridine or picoline ring, $R_3$ is hydrogen, unsubstituted or substituted $C_{1-4}$-alkyl or $C_{3-4}$-alkenyl, or together with $R_1$ and $R_2$ is a pyridine or picoline ring, $R_4$ is hydrogen or unsubstituted or substituted $C_{1-6}$-alkyl, n is the number 0 or 1 and $A^\ominus$ is a colourless anion, and the benzene nuclei B and C can also be substituted by non-chromophoric substituents.

4. A distyrylbenzene according to claim 2, of the formula

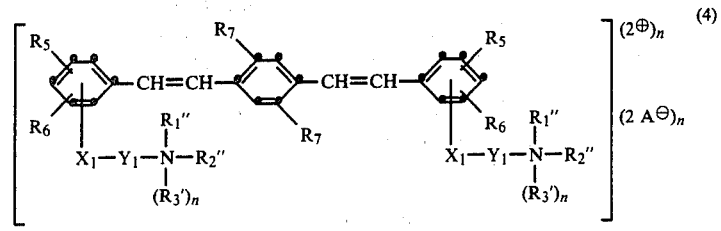

(4)

in which $X_1$ is —COO— or —CONH— in the o-position or a direct bond, oxygen, sulfur, —O—$C_{1-3}$-alkylene—CONH—, —SO$_2$NH—, —O—$C_{1-3}$-alkylene—COO— or —OCO—, $Y_1$ is $C_{1-4}$-alkylene or hydroxypropylene, $R_1''$ and $R_2''$ independently of one another are $C_{1-4}$-alkyl, together are a pyrrolidine, piperidine, hexamethyleneimine or morpholine ring or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1''$ and $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl or $C_{1-3}$-alkoxy, or together with $R_5$ is a trimethylene or tetramethylene group, $R_7$ is hydrogen, chlorine or methyl, n is the number 0 or 1 and $A^\ominus$ is a colourless anion.

5. A distyrylbenzene according to claim 4, of the formula

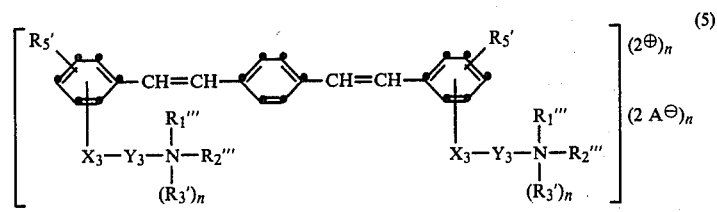

(5)

in which $X_3$ is a direct bond, oxygen, sulfur, —SO$_2$NH or —OCO—, $Y_3$ is $C_{1-4}$-alkylene, $R_1'''$ and $R_2'''$ independently of one another are $C_{1-4}$-alkyl, together are a pyrrolidine, piperidine or morpholine ring, or together with $R_3'$ are a pyridine ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1'''$ and $R_2'''$ is a pyridine ring, $R_5'$ is hydrogen, chlorine, $C_{1-4}$-alkyl or $C_{1-3}$-alkoxy, n is the number 0 or 1 and $A^\ominus$ is a colourless anion.

6. A distyrylbenzene according to claim 4, of the formula

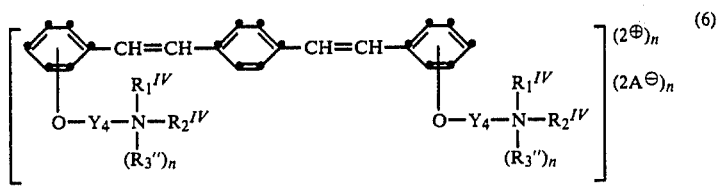

in which $Y_4$ is $C_{2-4}$-alkylene, $R_1^{IV}$ is $C_{1-3}$-alkyl or together with $R_2^{IV}$ is a pyrrolidine, piperidine, hexamethyleneimine or morpholine ring, $R_2^{IV}$ is $C_{1-3}$-alkyl or together with $R_1^{IV}$ is a pyrrolidine, piperidine, hexamethyleneimine or morpholine ring, $R_3''$ is hydrogen or $C_{1-3}$-alkyl, n is the number 0 or 1 and $A^\ominus$ is a colourless anion.

7. A distyrylbenzene according to claim 3, of the formula

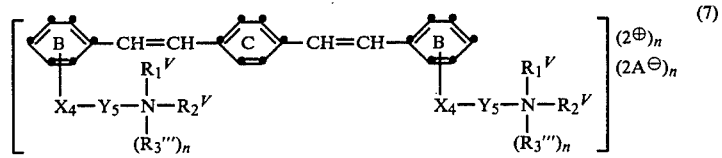

in which $X_4$ is oxygen, sulfur, —OCO—, —COO— or

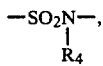

$Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{3-4}$-alkenyl, or together with $R_1^V$ is a heterocyclic ring, $R_3'''$ is hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents.

8. A distyrylbenzene according to claim 7, of the formula

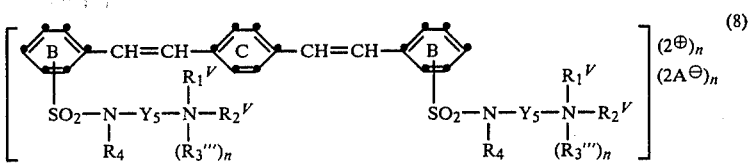

in which $Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{2-4}$-alkenyl, or together with $R_1^V$ is a heterocyclic ring, $R_3'''$ is hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents.

9. A distyrylbenzene according to claim 7, of the formula

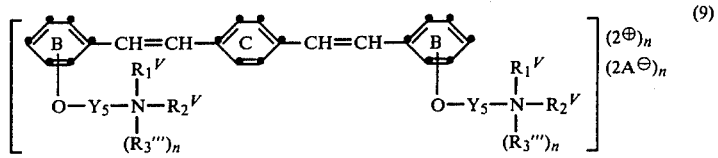

in which $Y_5$ is $C_{2-20}$-alkylene, $R_1^V$ is unsubstituted or substituted $C_{1-8}$-alkyl or $C_{3-4}$-alkenyl, or together with $R_2^V$ is a heterocyclic ring, $R_2^V$ is unsubstituted or substituted $C_{1-8}$-alkyl or $C_{2-4}$-alkenyl, or together with $R_1^V$ is a heterocyclic ring, $R_3'''$ is hydrogen or unsubstituted or substituted $C_{1-4}$-alkyl, $R_4$ is hydrogen or unsubstituted or substituted $C_{1-6}$-alkyl, $A^\ominus$ is a colourless anion and n is the number 0 or 1, and the benzene nuclei B and C can also be substituted by non-chromophoric substituents.

10. A distyrylbenzene according to claim 8, of the formula

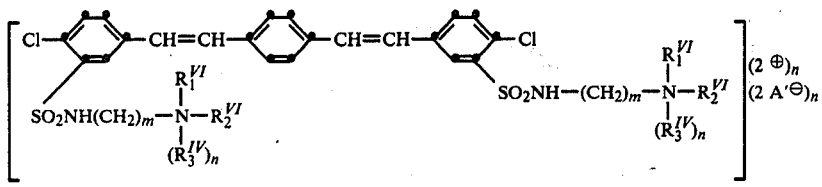

in which $R_1^{VI} = R_2^{VI}$ and both are methyl or ethyl, $R_3^{IV}$ is hydrogen, methyl or ethyl, $A'^{\ominus}$ is $CH_3OSO_3^{\ominus}$, $C_2H_5OSO_3^{\ominus}$ or

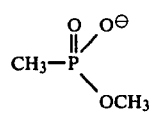, n is the number 0 or 1 and m is the number 2 or 3.

11. A distyrylbenzene according to claim 10, of the formula

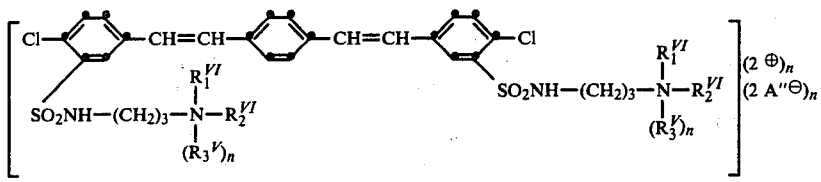

in which $R_1^{VI} = R_2^{VI}$ and both are methyl or ethyl, $R_3^V$ is hydrogen or methyl, $A''^{\ominus}$ is $CH_3OSO_3^{\ominus}$ or

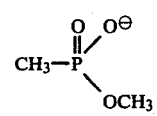

and n is the number 0 or 1.

12. A distyrylbenzene according to claim 11, of the formula

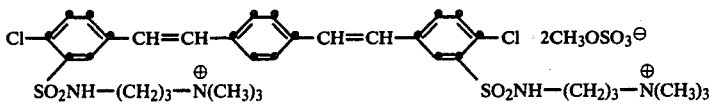

13. A distyrylbenzene according to claim 9, of the formula

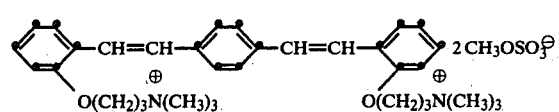

14. A distyrylbenzene according to claim 9, of the formula

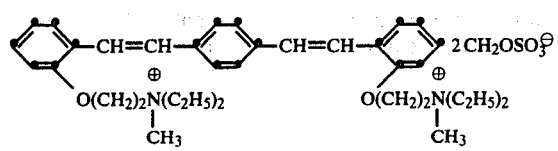

15. A distyrylbenzene according to claim 9, of the formula

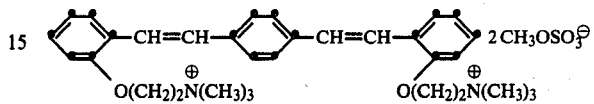

16. A process for the preparation of a distyrylbenzene of the formula (1)

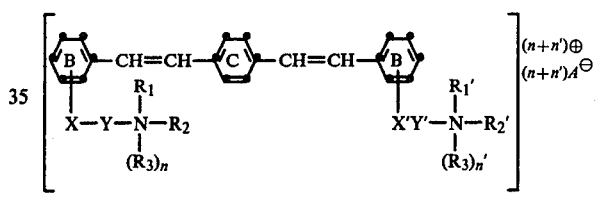

in which X and X' independently of one another are —COO— or —CON(R₄)— in the o-position, a direct bond, oxygen, sulfur, —O—C$_{1-3}$-alkylene—CON(R$_4$)—, —SO$_2$N(R$_4$)—, —O—C$_{1-3}$-alkylene—COO— or —OCO—, Y and Y' independently of one another are C$_{1-20}$-alkylene, R$_1$ and R$_1'$ independently of one another are unsubstituted or substituted C$_{1-8}$-alkyl or C$_{2-4}$-alkenyl, or R$_1$ together with R$_2$, or R$_1'$ together with R$_2'$, is a heterocyclic ring, R$_2$ and R$_2'$ independently of one another are unsubstituted or substituted C$_{1-8}$-alkyl or C$_{2-4}$-alkenyl, or R$_2$ together with R$_1$, or R$_2'$ together with R$_1'$, is a heterocyclic ring, or R$_1$ and R$_2$, or R$_1'$ and R$_2'$, together with R$_3$ are a pyridine or picoline ring, R$_3$ is hydrogen, unsubstituted or substituted C$_{1-4}$-alkyl or C$_{3-4}$-alkenyl, or together with R$_1$ and R$_2$ or with R$_1'$ and R$_2'$ is a pyridine or picoline ring, R$_4$ is hydrogen or unsubstituted or substituted C$_{1-6}$-alkyl, A$^{\ominus}$ is a colourless anion and n and n' independently of one another are the number 0 or 1, and the benzene nuclei B and C can also be substituted by non-chromophoric substituents, which comprises quaternising or protonising 1 mol equivalent of a distyrylbenzene of the formula

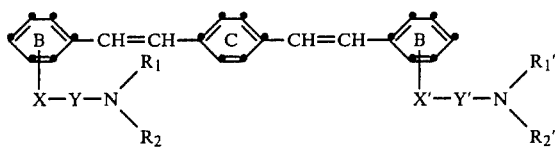

with 1 or 2 mol equivalents of an alkylating agent or respectively of an acid of the formula $R_3$—A, in which formulae the benzene nuclei B and C and X, X', Y, Y', $R_1$, $R_1'$, $R_2$, $R_2'$, $R_3$ and A are as defined above.

17. A process for the preparation of a distyrylbenzene of the formula

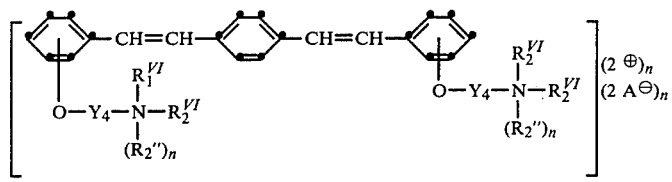

in which $Y_4$ is $C_{2-4}$-alkylene, $R_1^{IV}$ is $C_{1-3}$-alkyl or together with $R_2^{IV}$ is a pyrrolidine, piperidine, hexamethyleneimine or morpholine ring, $R_2^{IV}$ is $C_{1-3}$-alkyl or together with $R_1^{IV}$ is a pyrrolidine, piperidine, hexamethyleneimine or morpholine ring, $R_3''$ is hydrogen or $C_{1-3}$-alkyl, n is the number 0 or 1 and $A^\ominus$ is a colourless anion, which comprises reacting a compound of the formula

in a molecular ratio of 1:2 with a compound of the formula

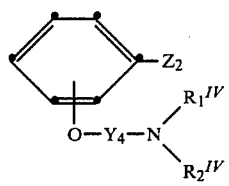

in the presence of a strong base, in which formulae $Y_4$, $R_1^{IV}$ and $R_2^{IV}$ are as defined above and one of the symbols $Z_1$ and $Z_2$ is an OCH group and the other is a grouping of the formula

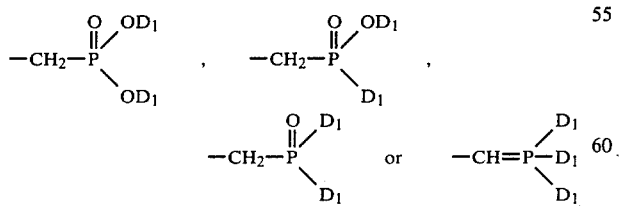

in which $D_1$ is an unsubstituted or substituted alkyl, aryl, cycloalkyl or aralkyl radical, and, if desired, quaternising or protonising the resulting compound of the formula

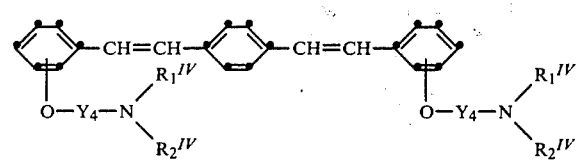

with 2 mol equivalents of an alkylating agent or respectively of an acid of the formula $R_3''$—A, in which formulae $Y_4$, $R_1^{IV}$, $R_2^{IV}$, $R_3''$ and A are as defined above.

18. A process for the fluorescent brightening of organic material, which comprises incorporating a distyrylbenzene of the formula (1) into this material or applying such a distyrylbenzene to the surface of the said material.

19. A process according to claim 18, for the fluorescent brightening of polyacrylonitrile or cellulose, as the organic material.

20. A detergent containing one or more distyrylbenzenes of the formula (1) defined in claim 1.

21. A detergent according to claim 20, which contains 10 to 70% by weight of a non-ionic surfactant and 1 to 30% by weight of a cationic textile softener.

22. A detergent according to claim 21, which contains 10 to 70% by weight of a non-ionic surfactant and 1 to 30% by weight of a quaternary derivative of ammonia and/or of imidazoline with 2 long-chain, aliphatic, saturated or unsaturated radicals, as the cationic textile softener, and also a solvent to render it in the liquid form.

23. A detergent according to claim 22, which contains 1-methyl-1-oleylamidoethyl-2-oleyl-imidazolinium·$X^\ominus$, 1-methyl-1-tallow-amidoethyl-2-tallow-imidazolinium·$X^\ominus$, di-tallow-dimethyl-ammonium·$X^\ominus$ or a compound of the formula

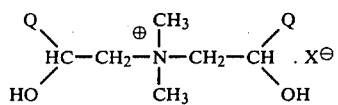

in which Q is $C_{14-16}$-alkyl and $X^\ominus$ is a chloride, bromide, methylsulfate, ethylsulfate, methanesulfonate, ethanesulfonate or toluenesulfonate anion, as the cationic textile softener.

24. A textile treatment agent containing one or more distyrylbenzenes of the formula (1) defined in claim 1.

25. A laundry after-treatment agent containing one or more distyrylbenzenes of the formula (1) defined in claim 1 and a cationic textile softener.

* * * * *